US010209173B2

(12) United States Patent
Sugiyama et al.

(10) Patent No.: US 10,209,173 B2
(45) Date of Patent: Feb. 19, 2019

(54) PARTICULATE SENSOR

(71) Applicant: NGK Spark Plug Co., LTD., Nagoya (JP)

(72) Inventors: Takeshi Sugiyama, Ichinomiya (JP); Masayuki Motomura, Komaki (JP); Norimasa Osawa, Inuyama (JP); Keisuke Tashima, Kasugai (JP); Toshiya Matsuoka, Kaizu (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 68 days.

(21) Appl. No.: 15/305,320

(22) PCT Filed: Aug. 21, 2015

(86) PCT No.: PCT/JP2015/073595
§ 371 (c)(1),
(2) Date: Oct. 19, 2016

(87) PCT Pub. No.: WO2016/027894
PCT Pub. Date: Feb. 25, 2016

(65) Prior Publication Data
US 2017/0045435 A1    Feb. 16, 2017

(30) Foreign Application Priority Data
Aug. 22, 2014    (JP) ................ 2014-169805

(51) Int. Cl.
G01N 15/06    (2006.01)
G01N 33/00    (2006.01)
G01N 15/00    (2006.01)

(52) U.S. Cl.
CPC ..... *G01N 15/0656* (2013.01); *G01N 33/0027* (2013.01); *G01N 2015/0046* (2013.01)

(58) Field of Classification Search
CPC ....... B01D 3/28; B01D 53/18; B01F 3/04078; B01J 19/30; B01J 19/305; B01J 19/32;
(Continued)

(56) References Cited

U.S. PATENT DOCUMENTS

2006/0117737 A1* 6/2006 Ohsaki ................ F02D 41/0072
60/276
2012/0260636 A1* 10/2012 Hashida .................. F01N 11/00
60/276
(Continued)

FOREIGN PATENT DOCUMENTS

JP        60-39543 A    3/1985
JP        3-61564 U     6/1991
(Continued)

OTHER PUBLICATIONS

International Search Report dated Nov. 17, 2015 for the corresponding PCT Application No. PCT/JP2015/073595.

*Primary Examiner* — Randy Gibson
*Assistant Examiner* — Gedeon M Kidanu
(74) *Attorney, Agent, or Firm* — Leason Ellis LLP

(57) ABSTRACT

A particulate sensor includes: an inner metallic member which is maintained at a first potential and which has a gas introduction pipe into which a target gas is introduced; a tubular outer metallic member which surrounds the radially outer circumference of the inner metallic member and which is attached to a gas flow pipe to thereby be maintained at a ground potential; and an insulating spacer which is interposed between the inner metallic member and the outer metallic member so as to electrically insulate them from each other and which has a tubular gas contact portion which is exposed to the interior of the gas flow pipe and comes into contact with the gas under measurement. The insulating spacer has a heater for heating the gas contact portion. The (Continued)

heater includes a heat generation resistor embedded in the insulating spacer.

8 Claims, 16 Drawing Sheets

(58) Field of Classification Search
CPC ........ B01J 2219/246; B01J 2219/30223; B01J 2219/30238; B01J 2219/3085; B01J 2219/32237; B01J 2219/32268; B01J 2219/3306; B01J 2219/3325; F25J 3/049
See application file for complete search history.

(56) References Cited

U.S. PATENT DOCUMENTS

| 2012/0285219 | A1* | 11/2012 | Matuoka | F02D 41/1466 |
| | | | | 73/23.33 |
| 2012/0312074 | A1* | 12/2012 | Allmendinger | G01N 15/0656 |
| | | | | 73/23.31 |
| 2014/0352405 | A1* | 12/2014 | Motomura | G01N 15/0656 |
| | | | | 73/23.31 |

FOREIGN PATENT DOCUMENTS

| JP | 2013-3106 A | 1/2013 | |
| JP | 2013-170950 A | 9/2013 | |
| JP | WO 2013136745 A1 * | 9/2013 | ......... G01N 15/0656 |
| JP | 2014-10099 A | 1/2014 | |
| WO | WO-2013/136745 A | 9/2013 | |

* cited by examiner

PARTICULATE SENSOR

CROSS-REFERENCE TO RELATED PATENT APPLICATIONS

This application is a U.S. National Phase application under 35 U.S.C. § 371 of International Patent Application No. PCT/JP2015/073595, filed Aug. 21, 2015, and claims the benefit of Japanese Patent Application No. 2014-169805, filed on Aug. 22, 2014, all of which are incorporated herein by reference in their entireties. The International application was published in Japanese on Feb. 25, 2016 as International Publication No. WO/2016/027894 under PCT Article 21(2).

FIELD OF THE INVENTION

The present invention relates to a particulate sensor attached to a metal gas flow pipe through which a target gas containing particulates flows and which includes an inner metallic member having a gas introduction pipe into which the target gas is introduced.

BACKGROUND OF THE INVENTION

In an internal combustion engine (e.g., a diesel engine or a gasoline engine), exhaust gas therefrom may contain particulates such as soot. Such exhaust gas containing particulates is cleaned through collection of particulates by a filter. Also, when necessary, the filter is heated to a high temperature so as to remove, through burning, particulates accumulated on the filter. However, in the event of breakage of the filter or a like problem, unclean exhaust gas is directly emitted downstream of the filter. Thus, demand has been rising for a particulate sensor capable of detecting the amount of particulates contained in exhaust gas in order to directly measure the amount of particulates contained in exhaust gas and to detect malfunction of the filter.

Such a particulate sensor includes, for example, an inner metallic member having a gas introduction pipe, an outer metallic member, and an insulating spacer. The inner metallic member is maintained at a first potential different from a ground potential and is adapted to introduce exhaust gas into the gas introduction pipe. The outer metallic member is a tubular member which surrounds the radially outer circumference of the inner metallic member and which is attached to an exhaust pipe to thereby be maintained at the ground potential. The insulating spacer is a tubular member which is interposed between the inner metallic member and the outer metallic member so as to electrically insulate them from each other. A portion (gas contact portion) of the insulating spacer is exposed to the interior of the exhaust pipe and is to come into contact with exhaust gas flowing through the exhaust pipe. Such a particulate sensor is disclosed in, for example, Japanese Patent Application Laid-Open (kokai) No. 2014-10099.

Problem to be Solved by the Invention

However, the insulating spacer involves a problem in that, since, as mentioned above, the gas contact portion is in contact with exhaust gas flowing through the exhaust pipe, foreign substances (e.g., soot and water droplets) contained in exhaust gas may adhere to the gas contact portion. Adhesion of such foreign substances to the gas contact portion causes a deterioration in insulation of the insulating spacer; and accordingly, a deterioration in insulation between the inner metallic member maintained at the first potential and the outer metallic member maintained at the ground potential, potentially resulting in a failure to properly detect the amount of particulates contained in exhaust gas.

The present invention has been accomplished in view of the current situation, and an object of the invention is to provide a particulate sensor which restrains a deterioration in insulation of the insulating spacer interposed between the outer metallic member and the inner metallic member having the gas introduction pipe to thereby be able to properly detect the amount of particulates contained in a target gas.

SUMMARY OF THE INVENTION

One mode of the present invention for solving the above-described problem is a particulate sensor attached to a metal gas flow pipe through which a target gas containing particulates flows and which is maintained at a ground potential, the particulate sensor comprising an inner metallic member which is maintained at a first potential different from the ground potential and which has a gas introduction pipe into which the target gas is introduced, the particulate sensor further comprising a tubular outer metallic member which surrounds a radially outer circumference of the inner metallic member and which is attached to the gas flow pipe to thereby be maintained at the ground potential; and a tubular insulating spacer which is interposed between the inner metallic member and the outer metallic member so as to electrically insulate them from each other and which has a tubular gas contact portion which is exposed to the interior of the gas flow pipe and contacts the target gas flowing through the gas flow pipe. The insulating spacer has a heater that heats the gas contact portion, and the heater includes a heat generation resistor embedded in the insulating spacer.

According to this particulate sensor, the insulating spacer has the heater which can heat the gas contact portion. Thus, even when foreign substances (soot and water droplets) contained in a target gas adhere to the gas contact portion, the foreign substances can be removed (evaporated or burned out) by activating the heater. Therefore, this particulate sensor can recover or maintain the insulation of the insulating spacer interposed between the outer metallic member maintained at the ground potential and the inner metallic member having the gas introduction pipe and maintained at the first potential and thus can properly detect the amount of particulates contained in the target gas. Also, since the heat generation resistor serving as a heat generation portion of the heater is embedded in the insulating spacer, this particulate sensor can restrain a failure to properly energize the heater and a deterioration of the heat generation resistor which could otherwise result from adhesion of foreign substances such as soot to the heat generation resistor. Therefore, even in the case of use of the particulate sensor over a long period of time, heating by the heater can be maintained in a good condition.

As mentioned above, the "insulating spacer" is configured to have a portion (gas contact portion) which is exposed to the interior of the gas flow pipe to thereby contacts a target gas. Specifically, the insulating spacer is configured such that the "gas contact portion" is partially or entirely located radially inward of the inner circumferential surface of the gas flow pipe. Alternatively, the insulating spacer may be configured such that the "gas contact portion" faces the interior of the gas flow pipe but is entirely located radially outward of the inner circumferential surface of the gas flow pipe.

The above-described particulate sensor is preferably a particulate sensor in which the heater has paired first and second heater terminals electrically communicating with the heat generation resistor; and the first heater terminal is formed on a spacer contact surface which contacts the outer metallic member, and the first heater terminal electrically communicates with the outer metallic member.

The above-described particulate sensor is preferably a particulate sensor in which the spacer contact surface is an annular surface extending in a circumferential direction of the insulating spacer; and the first heater terminal is annularly formed on the spacer contact surface to extend in the circumferential direction of the insulating spacer and is in contact with the outer metallic member over the entire circumference thereof.

Any of the above-described particulate sensors is preferably a particulate sensor in which the insulating spacer has a tubular spacer main body formed of an insulating ceramic, and a laminar heater section covering an outer circumferential surface of the spacer main body and including the heater; and the laminar heater section includes, as the heat generation resistor, a laminar heat generation resistor extending in the circumferential direction of the insulating spacer and also includes a cover insulating layer which is formed of an insulating ceramic and covers the laminar heat generation resistor, wherein opposite end portions of the laminar heat generation resistor located on opposite sides in the circumferential direction are disposed to face each other in the circumferential direction and be close to each other.

The above-described particulate sensor is preferably a particulate sensor in which the laminar heat generation resistor of the laminar heater section is configured such that each of the opposite end portions of the laminar heat generation resistor generates a larger amount of heat per unit length in the circumferential direction as compared with a central portion of the laminar heat generation resistor located between the opposite end portions.

Any of the above-described two particulate sensors is preferably a particulate sensor in which the insulating spacer has an annular protrusion member which is formed of an inorganic insulating material, is gastightly fitted onto the laminar heater section, and protrudes outward in the radial direction of the insulating spacer.

Any of the above-described particulate sensors is preferably a particulate sensor in which the gas contact portion of the insulating spacer includes a separated portion which is separated from the inner metallic member located radially inward of the gas contact portion with an inner space formed therebetween and is separated from the outer metallic member located radially outward of the gas contact portion with an outer space formed therebetween; and the heat generation resistor of the insulating spacer is located in the separated portion.

Any of the above-described particulate sensors is preferably a particulate sensor in which ions generated by gaseous discharge are caused to adhere to the particulates contained in the target gas introduced into the interior of the gas introduction pipe to thereby produce charged particulates; and the amount of the particulates contained in the target gas is detected by using a signal current which flows between the first potential and the ground potential in accordance with the amount of the charged particulates.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION (First Embodiment)

Figure 1:
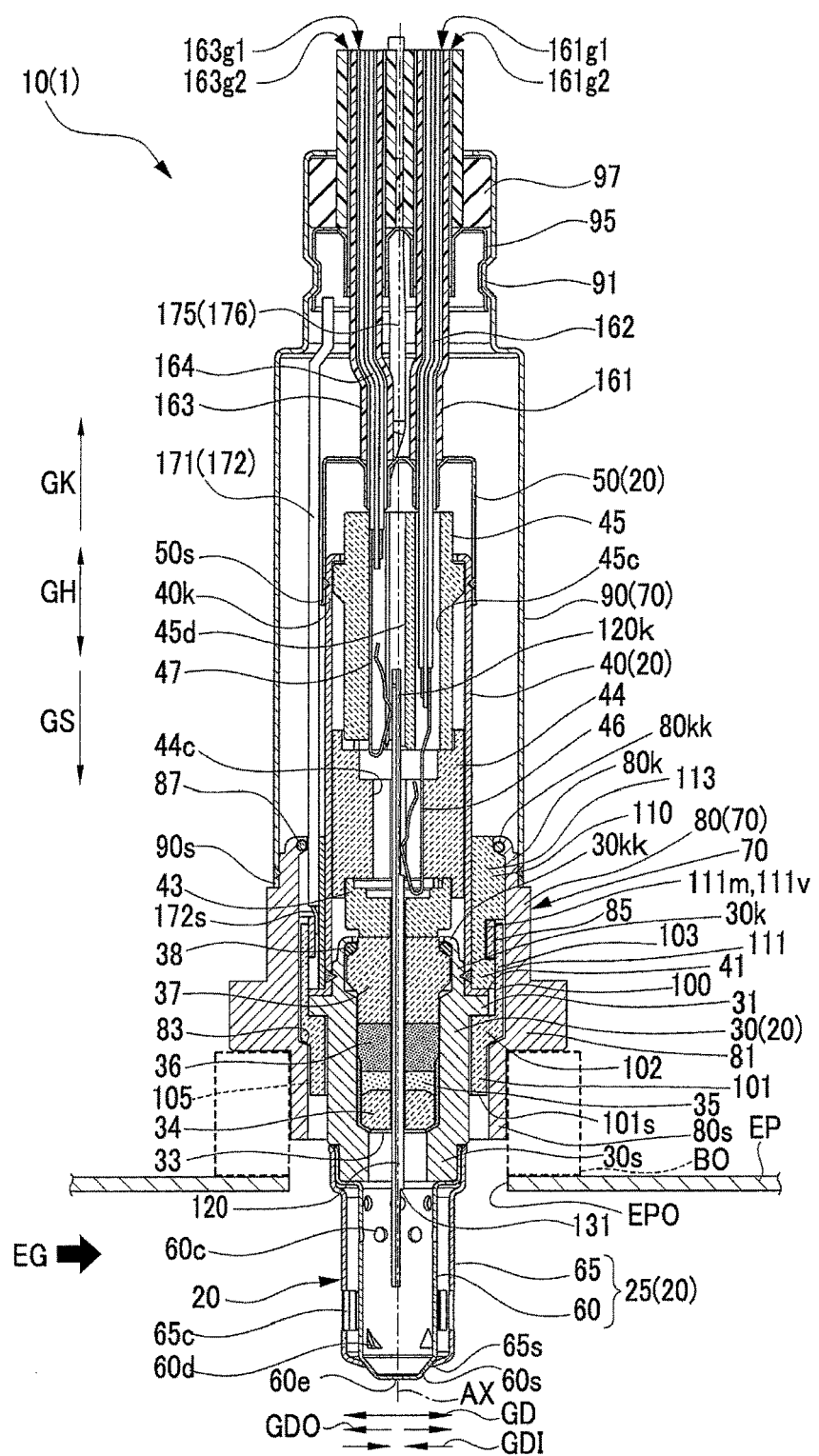
FIG. 1 is a longitudinal sectional view of a particulate sensor according to a first embodiment of the present invention.
Figure 2:
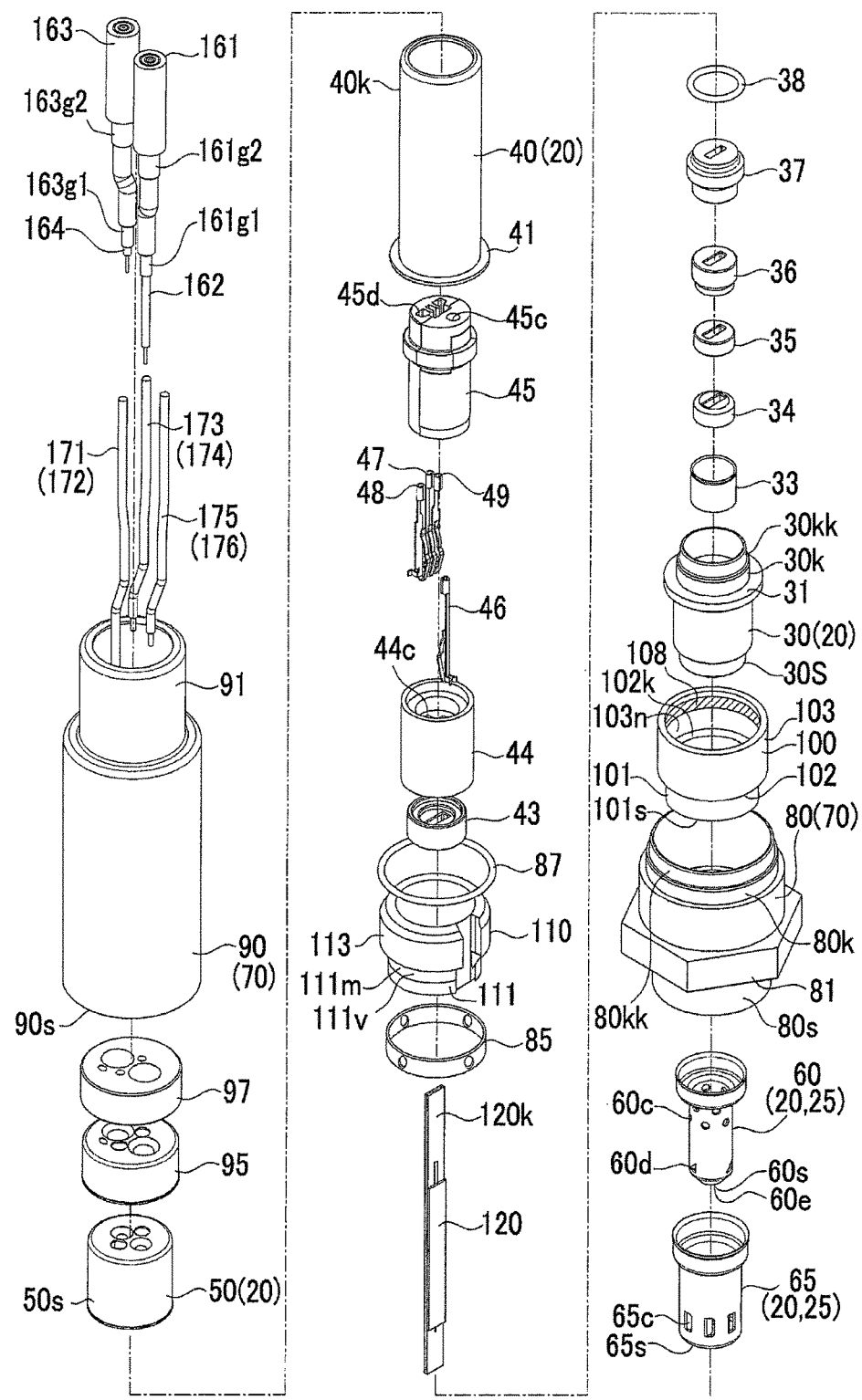
FIG. 2 is an exploded perspective view of the particulate sensor according to the first embodiment.
Figure 3:
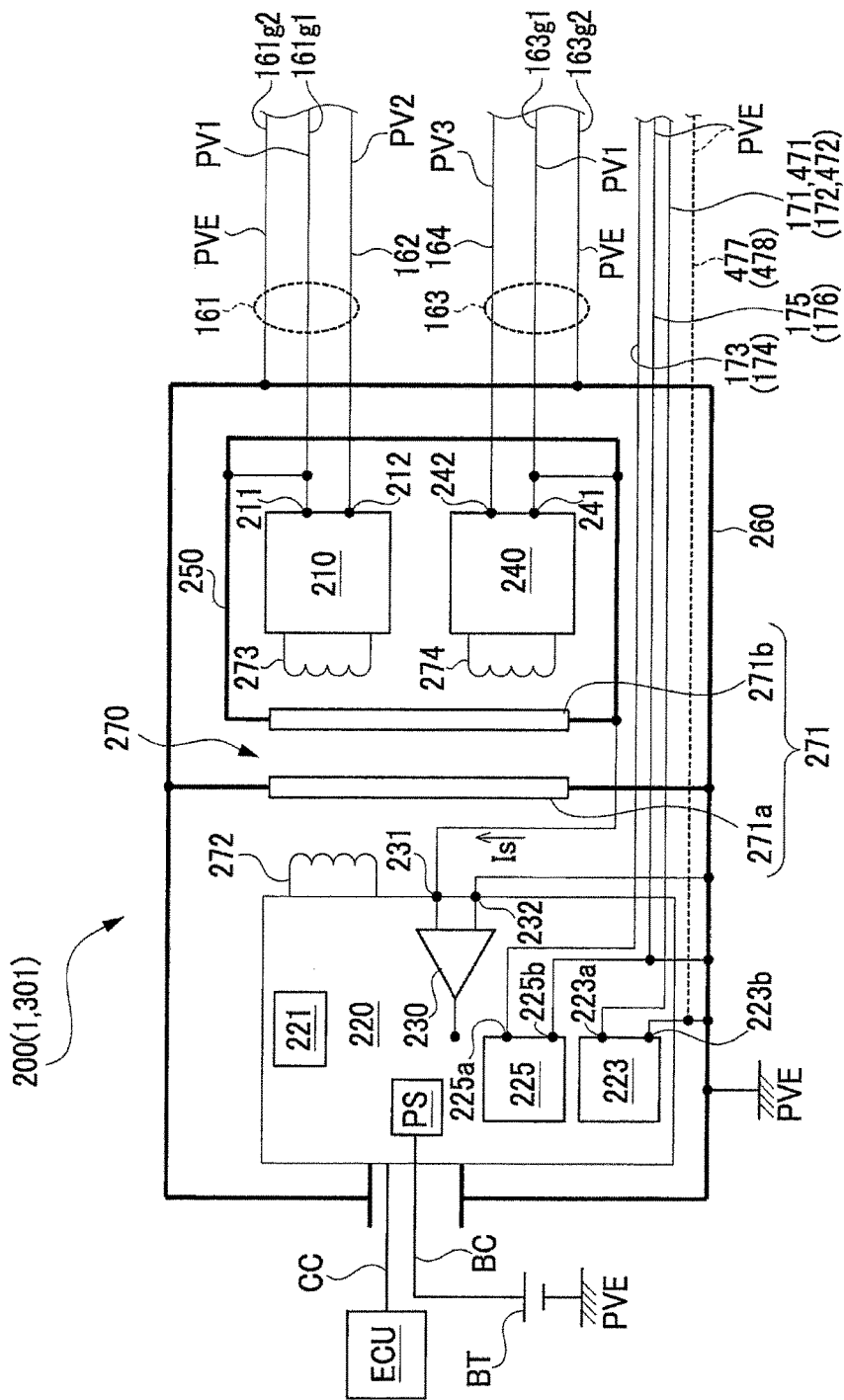
FIG. 3 is an explanatory view showing a schematic configuration of a circuit section of a particulate detection system according to the first embodiment or a second embodiment of the present invention.

A first embodiment of the present invention will be described with reference to the drawings. FIGS. 1 and 2 show a particulate sensor 10 of a particulate detection system 1. FIG. 3 shows a circuit section 200 of the particulate detection system 1. In FIG. 1, in a longitudinal direction GH along an axial line AX of the particulate sensor 10, a side (lower side in the drawing) on which a gas introduction pipe 25 is disposed corresponds to a distal end side GS, and a side (upper side in the drawing) which is opposite the distal end side GS and on which electric wires 161, 163, etc., extend corresponds to a proximal end side GK.

The particulate detection system 1 detects the amount of particulates S (soot, etc.) contained in exhaust gas (target gas) EG flowing through an exhaust pipe (gas flow pipe) EP of an internal combustion engine (engine). The particulate detection system 1 is composed of the particulate sensor 10 and the circuit section 200 according to the present embodiment.

First, the particulate sensor 10 is described (see FIGS. 1 and 2). The particulate sensor 10 is attached to the metal exhaust pipe EP maintained at a ground potential PVE. Specifically, the gas introduction pipe 25 serving as a distal end portion of an inner metallic member 20 of the particulate sensor 10 is disposed within the exhaust pipe EP through a mounting opening EPO provided in the exhaust pipe EP. Ions CP are caused to adhere to the particulates S contained in an introduced gas EGI introduced into the gas introduction pipe 25 through gas introduction holes 65c to thereby produce charged particulates SC, and the charged particulates SC, together with the introduced gas EGI, are discharged into the exhaust pipe EP through a gas discharge opening 60e (see FIG. 8). The particulate sensor 10 is composed of the inner metallic member 20 having the gas introduction pipe 25, an outer metallic member 70, a first insulating spacer 100, a second insulating spacer 110, a ceramic element 120, five electric wires 161, 163, 171, 173, and 175, etc.

The inner metallic member 20 electrically communicates with an inner circuit case 250 maintained at a first potential PV1, etc., of the circuit section 200 (to be described later) through inner-side outer conductors 161g1 and 163g1 of the electric wires 161 and 163 (to be described later) to thereby be maintained at the first potential PV1 different from the ground potential PVE. The inner metallic member 20 is composed of a metallic shell 30, an inner tube 40, an inner-tube metal connection member 50, and the gas introduction pipe 25 (an inner protector 60 and an outer protector 65).

The metallic shell 30 is a cylindrical stainless steel member extending in the longitudinal direction GH. The metallic shell 30 has an annular flange 31 projecting toward a radially outward side GDO; more specifically, toward an outward side in a radial direction GD orthogonal to the axial line AX. A metal cup 33 is disposed within the metallic shell 30. The metal cup 33 has a hole formed in its bottom wall, and the ceramic element 120, which will be described later, extends through the hole. In the interior of the metallic shell 30, around the ceramic element 120, a cylindrical ceramic holder 34 formed of alumina, first and second powder charged layers 35 and 36 formed by compressing powder of talc, and a cylindrical ceramic sleeve 37 formed of alumina are disposed in this order from the distal end side GS toward the proximal end side GK. Notably, the ceramic holder 34 and the first powder charged layer 35 are located within the metal cup 33. Further, a crimp portion 30kk, located furthest toward the proximal end side GK, of the metallic shell 30 is crimped toward a radially inward side GDI; i.e., inward in the radial direction GD, thereby pressing the ceramic sleeve 37 toward the distal end side GS through a crimp ring 38.

The inner tube 40 is a cylindrical stainless steel member extending in the longitudinal direction GH. A distal end portion of the inner tube 40 is formed into an annular flange 41 projecting toward the radially outward side GDO. The inner tube 40 is fitted onto a proximal end portion 30k of the metallic shell 30 and is laser-welded to the proximal end portion 30k with the flange 41 fitted to the flange 31.

In the interior of the inner tube 40, an insulating holder 43, a first separator 44, and a second separator 45 are disposed in this order from the distal end side GS toward the proximal end side GK. The insulating holder 43 is formed of a cylindrical insulating material and comes into contact with the ceramic sleeve 37 from the proximal end side GK. The ceramic element 120 extends through the insulating holder 43.

The first separator 44 is formed of an insulating material and has an insertion hole 44c. The insertion hole 44c allows the ceramic element 120 to extend therethrough and accommodates a distal end portion of a discharge potential terminal 46 therein. Within the insertion hole 44c, the discharge potential terminal 46 is in contact with a discharge potential pad 135 (to be described later; see FIGS. 6 and 7) of the ceramic element 120.

Meanwhile, the second separator 45 is formed of an insulating material and has a first insertion hole 45c and a second insertion hole 45d. A proximal end portion of the discharge potential terminal 46 accommodated within the first insertion hole 45c, and a distal end portion of a discharge potential lead wire 162 (to be described later) are connected to each other within the first insertion hole 45c. Within the second insertion hole 45d, an element proximal-end portion 120k of the ceramic element 120 is disposed; further, an auxiliary potential terminal 47, a heater terminal 48, and a heater terminal 49 are accommodated in a mutually insulated condition. Also, within the second insertion hole 45d, the auxiliary potential terminal 47 is in contact with an auxiliary potential pad 147 of the ceramic element 120; the heater terminal 48 is in contact with a heater pad 156 of the ceramic element 120; and the heater terminal 49 is in contact with a heater pad 158 of the ceramic element 120 (see also FIGS. 6 and 7). Further, within the second insertion hole 45d, distal end portions of an auxiliary potential lead wire 164, a heater lead wire 174, and a heater lead wire 176 (to be described later) are disposed. Within the second insertion hole 45d, the auxiliary potential terminal 47 and the auxiliary potential lead wire 164 are connected to each other; the heater terminal 48 and the heater lead wire 174 are connected to each other; and the heater terminal 49 and the heater lead wire 176 are connected to each other.

The inner-tube metal connection member 50 is a stainless steel member and is fitted onto a proximal end portion 40k of the inner tube 40 while surrounding a proximal end portion of the second separator 45, and a distal end portion 50s of the inner-tube metal connection member 50 is laser-welded to the proximal end portion 40k of the inner tube 40. The four electric wires 161, 163, 173, and 175 are passed through the inner-tube metal connection member 50. The electric wire 171 is not passed through the inner-tube metal connection member 50. Of these electric wires, the inner-side outer conductors 161g1 and 163g1 of the electric wires 161 and 163, which are triple coaxial cables as will be described later, are connected to the inner-tube metal connection member 50.

The gas introduction pipe 25 is composed of the inner protector 60 and the outer protector 65. The inner protector 60 is a closed-bottomed cylindrical member formed of stainless steel, and the outer protector 65 is a cylindrical member formed of stainless steel. The outer protector 65 is disposed around the inner protector 60 with respect to the radial direction GD. The inner protector 60 and the outer protector 65 are fitted onto a distal end portion 30s of the metallic shell 30 and are laser-welded to the distal end portion 30*s*. The gas introduction pipe 25 surrounds, from the radially outward side GDO, a distal end portion of the ceramic element 120 projecting from the metallic shell 30 toward the distal end side GS to thereby protect the ceramic element 120 from water droplets and foreign substances as well as introduce the exhaust gas EG to a space around the ceramic element 120.

The outer protector 65 has a plurality of the rectangular gas introduction holes 65*c* formed in a distal end portion thereof for introducing the exhaust gas EG into the interior thereof. Also, the inner protector 60 has a plurality of circular first inner introduction holes 60*c* formed in a proximal end portion thereof for introducing, into the interior thereof, the introduced gas EGI introduced into the outer protector 65. The inner protector 60 also has a plurality of triangular second inner introduction holes 60*d* formed in a distal end portion thereof. Further, the inner protector 60 has the circular gas discharge opening 60*e* formed in a bottom wall thereof for discharging the introduced gas EGI into the exhaust pipe EP, and its distal end portion 60*s*, including the gas discharge opening 60*e*, projects toward the distal end side GS from a distal end opening 65*s* of the outer protector 65.

Figure 8:
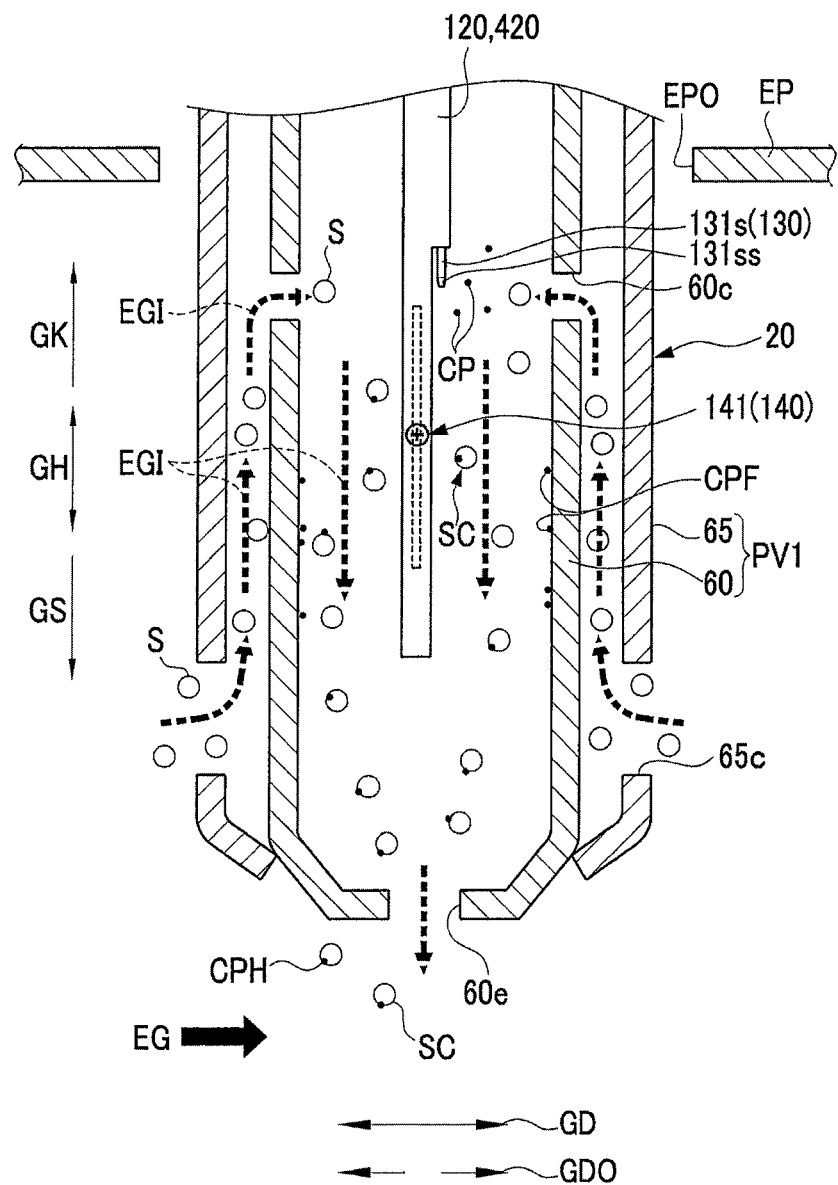
FIG. 8 is an explanatory view schematically showing introduction, charging, and discharge of particulates in the particulate sensor according to the first or second embodiment.

Here, there will be described the introduction and discharge of the exhaust gas EG into and from the interiors of the inner protector 60 and the outer protector 65 when the particulate sensor 10 is used (see FIG. 8). In FIG. 8, the exhaust gas EG flows within the exhaust pipe EP from the left-hand side toward the right-hand side. When the exhaust gas EG passes through a region around the outer protector 65 and the inner protector 60, its flow velocity increases on the outer side of the gas discharge opening 60*e* of the inner protector 60, and a negative pressure is produced near the gas discharge opening 60*e* due to the so-called Venturi effect.

By this negative pressure, the introduced gas EGI introduced into the inner protector 60 is discharged to the exhaust pipe EP through the gas discharge opening 60*e*. Simultaneously, the exhaust gas EG around the gas introduction holes 65*c* of the outer protector 65 is introduced into the interior of the outer protector 65 through the gas introduction holes 65*c*, and is further introduced into the interior of the inner protector 60 through the first inner introduction holes 60*c* of the inner protector 60. The introduced gas EGI within the inner protector 60 is discharged through the gas discharge opening 60*e*. Thus, as indicated by the broken line arrow, a flow of the introduced gas EGI from the first inner introduction holes 60*c* on the proximal end side GK toward the gas discharge opening 60*e* on the distal end side GS is produced within the inner protector 60.

Next, the outer metallic member 70 will be described. The outer metallic member 70 is formed of a cylindrical metal material, circumferentially surrounds the inner metallic member 20 from the radial direction GD while being separated from the inner metallic member 20, and is attached to the exhaust pipe EP maintained at the ground potential PVE to thereby be maintained at the ground potential PVE. The outer metallic member 70 is composed of a mounting metallic member 80 and an outer tube 90.

The mounting metallic member 80 is a cylindrical stainless steel member extending in the longitudinal direction GH. The mounting metallic member 80 is disposed around the metallic shell 30 and a distal end portion of the inner tube 40 of the inner metallic member 20 in such a manner as to be separated from them in the radial direction GD. The mounting metallic member 80 has a flange portion 81 which projects toward the radially outward side GDO so as to form a hexagonal outer shape. The mounting metallic member 80 has an internal stepped portion 83. The mounting metallic member 80 also has a male screw (not shown) used for fixation to the exhaust pipe EP and formed on the outer circumference of its distal end portion 80*s* located on the distal end side GS of the flange portion 81. By means of the male screw of the distal end portion 80*s*, the particulate sensor 10 is attached to an attachment boss BO which is formed of metal and is separately fixed to the exhaust pipe EP, whereby the particulate sensor 10 is fixed to the exhaust pipe EP via the attachment boss BO.

The first insulating spacer 100 and the second insulating spacer 110 (to be described later) are disposed between the mounting metallic member 80 and the inner metallic member 20. Further, a heater metal connection member 85 (to be described later) and a distal end portion 172*s* of a heater lead wire 172 of the electric wire 171 connected to the heater metal connection member 85 are disposed between the mounting metallic member 80 and the inner metallic member 20. A crimp portion 80*kk*, located furthest toward the proximal end side GK, of the mounting metallic member 80 is crimped toward the radially inward side GDI, thereby pressing the second insulating spacer 110 toward the distal end side GS through a line packing 87.

The outer tube 90 is a tubular stainless steel member extending in the longitudinal direction GH. A distal end portion 90*s* of the outer tube 90 is fitted onto a proximal end portion 80*k* of the mounting metallic member 80 and is laser-welded to the proximal end portion 80*k*. An outer-tube metal connection member 95 is disposed in the interior of a small diameter portion 91 of the outer tube 90 located on the proximal end side GK; further, a grommet 97 formed of fluororubber is disposed on the proximal end side GK of the outer-tube metal connection member 95 in the interior of the small diameter portion 91. The five electric wires 161, 163, 171, 173, and 175 (to be described later) are passed through the outer-tube metal connection member 95 and the grommet 97. Of these electric wires, outer-side outer conductors 161*g*2 and 163*g*2 of the electric wires 161 and 163, which are triple coaxial cables as will be described later, are connected to the outer-tube metal connection member 95. The outer-tube metal connection member 95 is crimped together with the small diameter portion 91 of the outer tube 90 so that the diameter of the outer-tube metal connection member 95 decreases toward the radially inward side GDI; thus, the outer-tube metal connection member 95 and the grommet 97 are fixed within the small diameter portion 91 of the outer tube 90.

Figure 4:
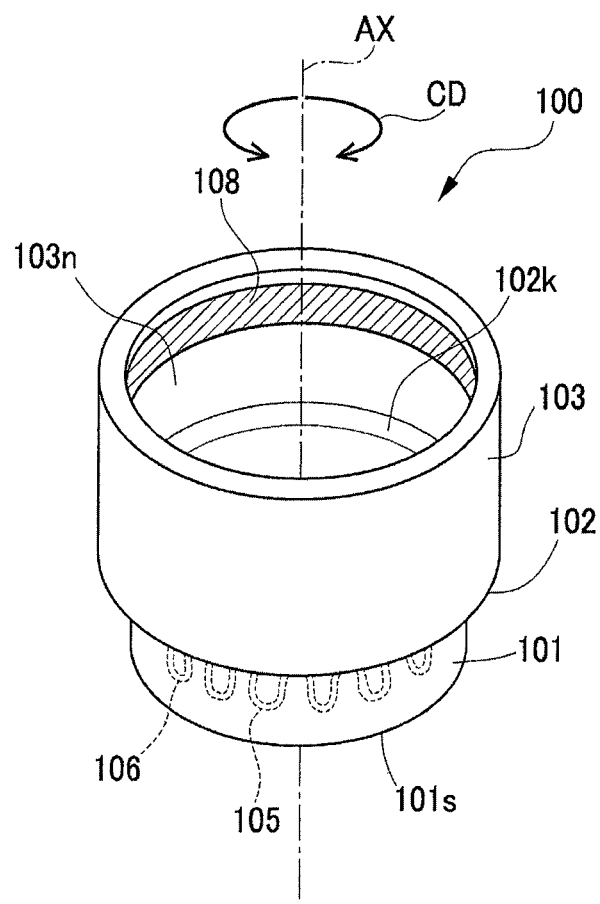
FIG. 4 is a perspective view of a first insulating spacer according to the first embodiment as viewed from a proximal end side.
Figure 5:
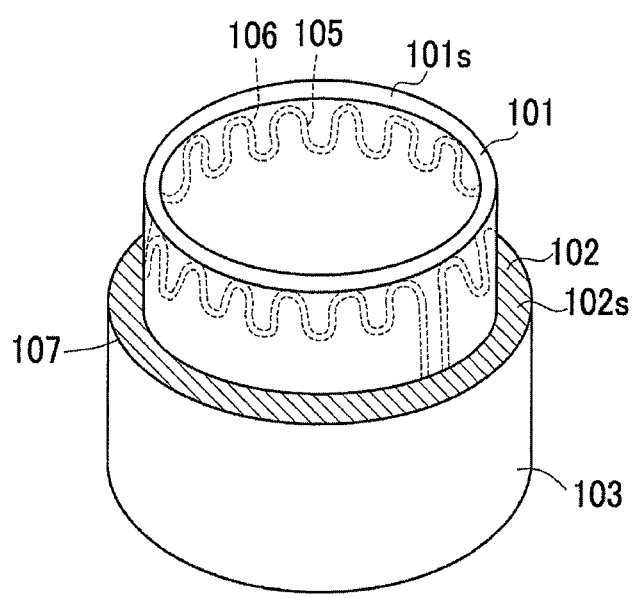
FIG. 5 is a perspective view of the first insulating spacer according to the first embodiment as viewed from a distal end side.

Next, the first insulating spacer 100 will be described (see also FIGS. 4 and 5). The first insulating spacer 100 is a cylindrical alumina member extending in the longitudinal direction GH. The first insulating spacer 100 is interposed between the inner metallic member 20 and the outer metallic member 70 so as to electrically insulate them from each other. Specifically, the first insulating spacer 100 is disposed between the mounting metallic member 80 of the outer metallic member 70 and the metallic shell 30 and a distal end portion of the inner tube 40 of the inner metallic member 20. The first insulating spacer 100 is composed of a spacer distal end portion 101 having a small diameter and located on the distal end side GS, a spacer proximal end portion 103 having a large diameter and located on the proximal end side GK, and a spacer intermediate portion 102 which connects the spacer distal end portion 101 and the spacer proximal end portion 103.

In a state in which the particulate sensor 10 is attached to the exhaust pipe EP, a distal end portion of the spacer distal end portion 101 is exposed to the interior of the exhaust pipe EP (faces the interior of the exhaust pipe EP) so as to serve as a gas contact portion 101s which comes into contact with the exhaust gas EG flowing through the exhaust pipe EP. The spacer intermediate portion 102 has an outer shoulder surface (spacer contact surface) 102s which faces the distal end side GS, and an inner shoulder surface 102k which faces the proximal end side GK. The outer shoulder surface 102s and the inner shoulder surface 102k are annular surfaces extending in a circumferential direction CD of the first insulating spacer 100. The outer shoulder surface 102s comes into contact with the stepped portion 83 of the mounting metallic member 80 from the proximal end side GK over the entire circumference thereof. Meanwhile, the flange 31 of the metallic shell 30 comes into contact with the inner shoulder surface 102k from the proximal end side GK.

The first insulating spacer 100 has a spacer heater 105 embedded therein and adapted to heat the gas contact portion 101s. Specifically, the spacer heater 105 has a heat generation resistor 106 formed of tungsten, and paired first heater terminal 107 and second heater terminal 108 electrically communicating with opposite ends of the heat generation resistor 106. The heat generation resistor 106 is embedded in the spacer distal end portion 101 in a meandering manner over the entire circumference thereof. The first heater terminal 107 is formed on the outer shoulder surface 102s of the spacer intermediate portion 102 and electrically communicates with the mounting metallic member 80. Specifically, the first heater terminal 107 is formed on the entire surface of the outer shoulder surface 102s in an annular manner extending in the circumferential direction CD of the first insulating spacer 100 to thereby come into contact with the stepped portion 83 of the mounting metallic member 80 over the entire circumference thereof.

Meanwhile, the second heater terminal 108 is formed on a proximal end portion of an inner circumferential surface 103n of the spacer proximal end portion 103 in a cylindrical manner extending in the circumferential direction CD of the first insulating spacer 100. The cylindrical heater metal connection member 85 is disposed on the radially inward side GDI of the spacer proximal end portion 103 and is in contact with the second heater terminal 108 formed on the inner circumferential surface 103n of the spacer proximal end portion 103n. The distal end portion 172s of the heater lead wire 172 of the electric wire 171 (to be described later) is connected to the heater metal connection member 85. The electric wire 171 extends in a region between the inner metallic member 20 and the outer metallic member 70 from the heater metal connection member 85 toward the proximal end side GK and extends to the outer side of the outer metallic member 70.

Next, the second insulating spacer 110 will be described. The second insulating spacer 110 is a tubular alumina member extending in the longitudinal direction GH. The second insulating spacer 110 is interposed between the inner metallic member 20 and the outer metallic member 70 so as to electrically insulate them from each other. Specifically, the second insulating spacer 110 is disposed between a distal end portion of the inner tube 40 of the inner metallic member 20 and the mounting metallic member 80 of the outer metallic member 70. The second insulating spacer 110 is composed of a distal end portion 111 located on the distal end side GS and a proximal end portion 113 located on the proximal end side GK.

The distal end portion 111 is smaller in outside diameter and thickness than the proximal end portion 113. The distal end portion 111 is disposed between the inner tube 40 and the spacer proximal end portion 103 of the first insulating spacer 100. A groove 111v extending in the circumferential direction of the second insulating spacer 110 is formed on an outer circumferential surface 111m of the distal end portion 111 over the entire circumference thereof, and the aforementioned heater metal connection member 85 is disposed in the groove 111v. Meanwhile, the proximal end portion 113 is located on the proximal end side GK of the spacer proximal end portion 103 of the first insulating spacer 100 and is disposed between the mounting metallic member 80 and the inner tube 40.

As mentioned above, the crimp portion 80kk of the mounting metallic member 80 presses the second insulating spacer 110 toward the forward end side GS through the line packing 87. Thus, the distal end portion 111 of the second insulating spacer 110 presses the flange 41 of the inner tube 40 and the flange 31 of the metallic shell 30 toward the distal end side GS. Further, these flanges 41 and 31 press the spacer intermediate portion 102 of the first insulating spacer 100 toward the distal end side GS, whereby the spacer intermediate portion 102 is engaged with the stepped portion 83 of the mounting metallic member 80. Thus, the first insulating spacer 100 and the second insulating spacer 110 are fixed between the inner metallic member 20 (the metallic shell 30 and a distal end portion of the inner tube 40) and the outer metallic member 70 (mounting metallic member 80).

Figure 6:
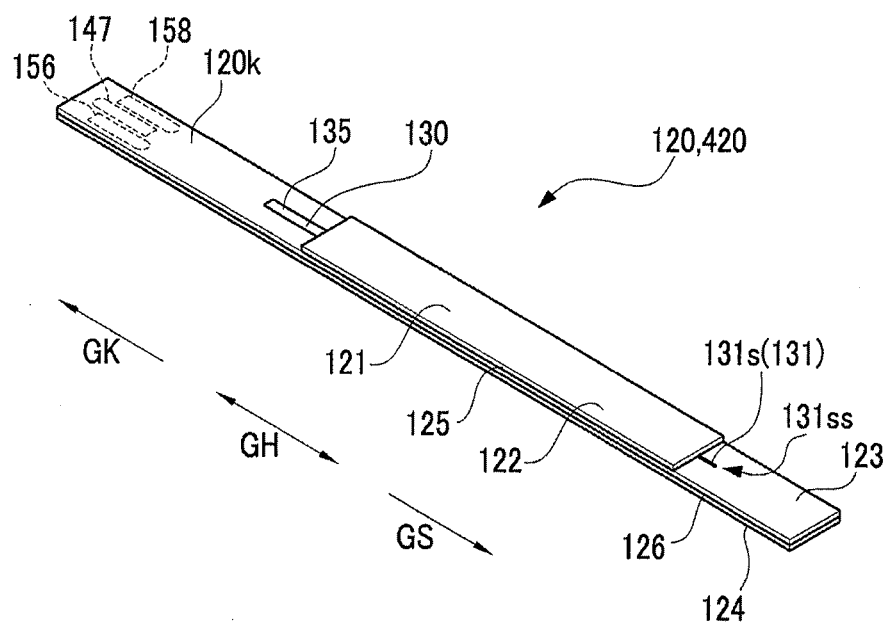
FIG. 6 is a perspective view of a ceramic element according to the first or second embodiment.
Figure 7:
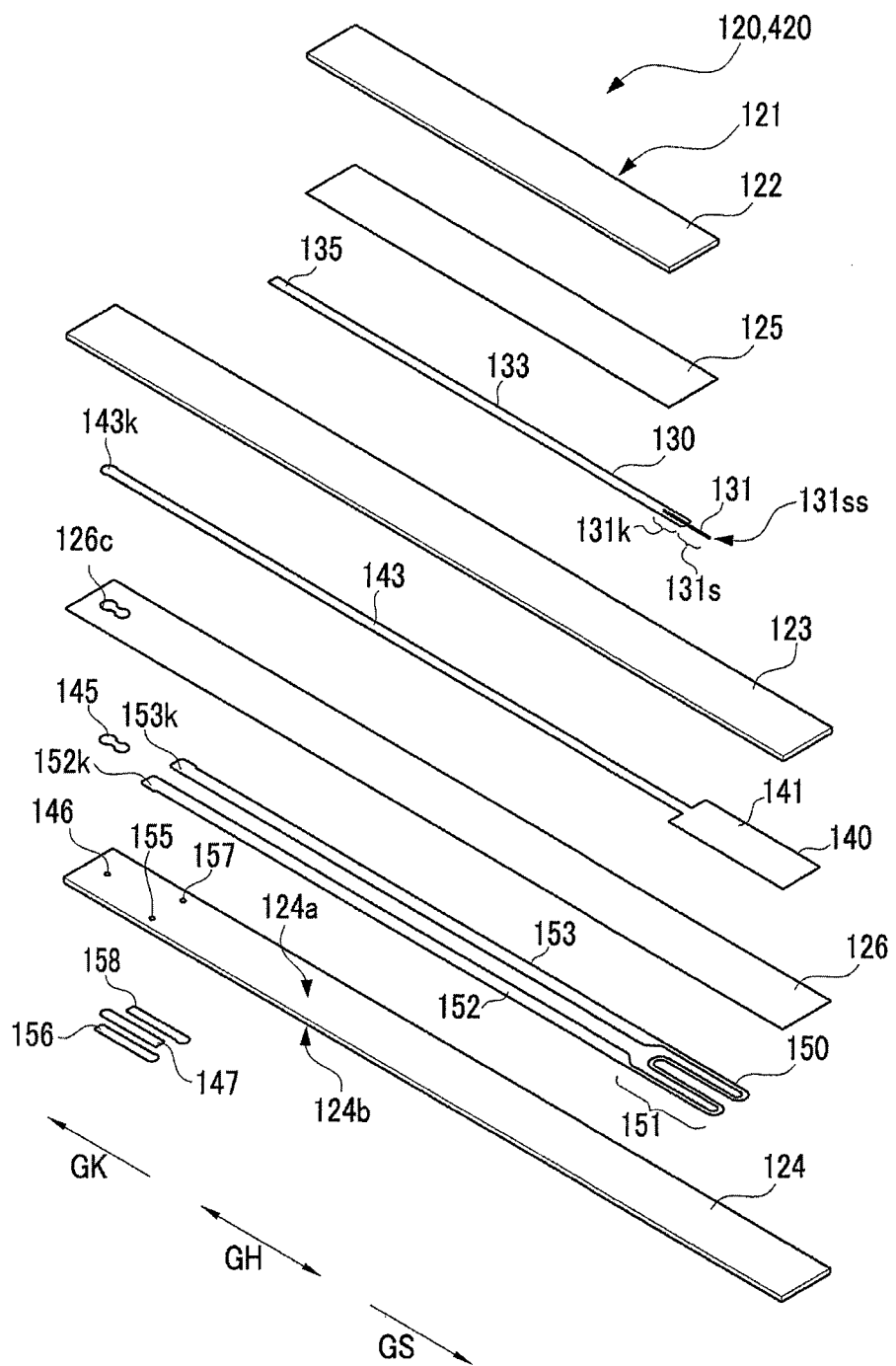
FIG. 7 is an exploded perspective view of the ceramic element according to the first or second embodiment.

Next, the ceramic element 120 will be described (see also FIGS. 6 and 7). The ceramic element 120 has a plate-shaped insulative ceramic substrate 121 formed of alumina and extending in the longitudinal direction GH. A discharge electrode member 130, an auxiliary electrode member 140, and an element heater 150 are embedded in the ceramic substrate 121, and are integrated through firing (integral firing). Specifically, the ceramic substrate 121 is a ceramic laminate in which three ceramic layers 122, 123, and 124 formed of alumina originating from an alumina green sheet are layered together, and two insulating cover layers 125 and 126 of alumina are formed between these layers by means of printing. The ceramic layer 122 and the insulating cover layer 125 are shorter than the ceramic layers 123 and 124 and the insulating cover layer 126 as measured on the distal end side GS and the proximal end side GK in the longitudinal direction GH. The discharge electrode member 130 is disposed between the insulating cover layer 125 and the ceramic layer 123. Also, the auxiliary electrode member 140 is disposed between the ceramic layer 123 and the insulating cover layer 126, and the element heater 150 is disposed between the insulating cover layer 126 and the ceramic layer 124.

The discharge electrode member 130 extends in the longitudinal direction GH and is composed of a needle-shaped electrode portion 131 located at the distal end side GS, a discharge potential pad 135 located at the proximal end side GK, and a lead portion 133 extending therebetween. The needle-shaped electrode portion 131 is formed of a platinum wire. Meanwhile, the lead portion 133 and the discharge potential pad 135 are formed of tungsten by means of pattern printing. A proximal end portion 131k of the needle-shaped electrode portion 131 and the lead portion 133 of the discharge electrode member 130 are entirely embedded in the ceramic substrate 121. Meanwhile, a distal end portion 131s of the needle-shaped electrode portion 131 projects from the ceramic substrate 121 on the distal end side GS of the ceramic layer 122 of the ceramic substrate 121. Also, the discharge potential pad 135 is exposed from the ceramic substrate 121 on the proximal end side GK of the ceramic layer 122 of the ceramic substrate 121. As mentioned above, the discharge potential terminal 46 is in contact with the discharge potential pad 135 within the insertion hole 44c of the first separator 44.

The auxiliary electrode member 140 extends in the longitudinal direction GH, is formed by means of pattern printing, and is entirely embedded in the ceramic substrate 121. The auxiliary electrode member 140 is composed of a rectangular auxiliary electrode portion 141 located at the distal end side GS and a lead portion 143 connected to the auxiliary electrode portion 141 and extending toward the proximal end side GK. A proximal end portion 143k of the lead portion 143 is connected to a conductor pattern 145 formed on one main surface 124a of the ceramic layer 124 through a through hole 126c of the insulating cover layer 126. Further, the conductor pattern 145 is connected to the auxiliary potential pad 147 formed on the other main surface 124b of the ceramic layer 124 via a through hole conductor 146 formed in the ceramic layer 124 in such a manner as to extend therethrough. As mentioned above, the auxiliary potential terminal 47 is in contact with the auxiliary potential pad 147 within the second insertion hole 45d of the second separator 45.

The element heater 150 is formed by means of pattern printing and is entirely embedded in the ceramic substrate 121. The element heater 150 is composed of a heat generation resistor 151 located at the distal end side GS for heating the ceramic element 120, and paired heater lead portions 152 and 153 connected to the opposite ends of the heat generation resistor 151 and extending toward the proximal end side GK. A proximal end portion 152k of one heater lead portion 152 is connected to the heater pad 156 formed on the other main surface 124b of the ceramic layer 124 via a through hole conductor 155 formed in the ceramic layer 124 in such a manner as to extend therethrough. As mentioned above, the heater terminal 48 is in contact with the heater pad 156 within the second insertion hole 45d of the second separator 45. Also, a proximal end portion 153k of the other heater lead portion 153 is in contact with the heater pad 158 formed on the other main surface 124b of the ceramic layer 124 via a through hole conductor 157 formed in the ceramic layer 124 in such a manner as to extend therethrough. As mentioned above, the heater terminal 49 is in contact with the heater pad 158 within the second insertion hole 45d of the second separator 45.

Next, the electric wires 161, 163, 171, 173, and 175 will be described. Of these five electric wires, the two electric wires 161 and 163 are triple coaxial cables (triaxial cables), and the remaining three electric wires 171, 173, and 175 are small-diameter single-core insulated electric wires.

Of these electric wires, the electric wire 161 has the discharge potential lead wire 162 as a core wire (center conductor). As mentioned above, the discharge potential lead wire 162 is connected to the discharge potential terminal 46 within the first insertion hole 45c of the second separator 45. Also, the electric wire 163 has the auxiliary potential lead wire 164 as a core wire (center conductor). The auxiliary potential lead wire 164 is connected to the auxiliary potential terminal 47 within the second insertion hole 45d of the second separator 45. Of the coaxial double outer conductors of the electric wires 161 and 163, the inner-side outer conductors 161g1 and 163g1 located on the inner side are connected to the inner-tube metal connection member 50 of the inner metallic member 20 to thereby be maintained at the first potential PV1. Meanwhile, the outer-side outer conductors 161g2 and 163g2 located on the outer side are connected to the outer-tube metal connection member 95 electrically communicating with the outer metallic member 70 to thereby be maintained at the ground potential PVE.

Also, the electric wire 171 has the heater lead wire 172 as a core wire. The heater lead wire 172 is, as mentioned above, connected to the heater metal connection member 85 in the interior of the mounting metallic member 80. The electric wire 173 has the heater lead wire 174 as a core wire. The heater lead wire 174 is connected to the heater terminal within the second insertion hole 45d of the second separator 45. The electric wire 175 has the heater lead wire 176 as a core wire. The heater lead wire 176 is connected to the heater terminal 49 within the second insertion hole 45d of the second separator 45.

Next, the circuit section 200 will be described (see FIG. 3). The circuit section 200 has a circuit which is connected to the electric wires 161, 163, 171, 173, and 175 of the particulate sensor 10 and which drives the particulate sensor 10 and detects a signal current Is (to be described later). The circuit section 200 has an ion source power supply circuit 210, an auxiliary electrode power supply circuit 240, and a measurement control circuit 220.

The ion source power circuit 210 has a first output terminal 211 maintained at the first potential PV1 and a second output terminal 212 maintained at a second potential PV2. The second potential PV2 is a positive high potential in relation to the first potential PV1. The auxiliary electrode power supply circuit 240 has an auxiliary first output terminal 241 maintained at the first potential PV1 and an auxiliary second output terminal 242 maintained at an auxiliary electrode potential PV3. The auxiliary electrode potential PV3 is a positive high DC potential in relation to the first potential PV1, but is lower than a peak potential of the second potential PV2.

The measurement control circuit 220 has a signal current detection circuit 230, a first heater energization circuit 223, and a second heater energization circuit 225. The signal current detection circuit 230 has a signal input terminal 231 maintained at the first potential PV1 and a ground input terminal 232 maintained at the ground potential PVE. The ground potential PVE and the first potential PV1 are insulated from each other, and the signal current detection circuit 230 detects the signal current Is flowing between the signal input terminal 231 (first potential PV1) and the ground input terminal 232 (ground potential PVE).

The first heater energization circuit 223 energizes the spacer heater 105 of the first insulating spacer 100 by PWM control for heating the spacer heater 105 and has an energization terminal 223a connected to the heater lead wire 172 of the electric wire 171 and an energization terminal 223b maintained at the ground potential PVE. The second heater energization circuit 225 energizes the element heater 150 of the ceramic element 120 by PWM control so as to cause the element heater 150 to generate heat and has an energization terminal 225a connected to the heater lead wire 174 of the electric wire 173 and an energization terminal 225b connected to the heater lead wire 176 of the electric wire 175 and maintained at the ground potential PVE.

In the circuit section 200, the ion source power supply circuit 210 and the auxiliary electrode power supply circuit 240 are surrounded by an inner circuit case 250 maintained at the first potential PV1. Also, the inner circuit case 250 accommodates and surrounds a secondary iron core 271b of an insulated transformer 270 and electrically communicates with the inner-side outer conductors 161g1 and 163g1 maintained at the first potential PV1 of the electric wires 161 and 163. The insulated transformer 270 is configured such that its iron core 271 is separated into a primary iron core 271a having a primary coil 272 wound thereon and the secondary iron core 271b having a power-supply-circuit-side coil 273 and an auxiliary-electrode-power-supply-side coil 274 wound thereon. The primary iron core 271a electrically communicates with the ground potential PVE, and the secondary iron core 271b electrically communicates with the first potential PV1.

Further, the ion source power supply circuit 210, the auxiliary electrode power supply circuit 240, the inner circuit case 250, and the measurement control circuit 220 are surrounded by an outer circuit case 260 maintained at the ground potential PVE. Also, the outer circuit case 260 accommodates and surrounds the primary iron core 271a of the insulated transformer 270 and electrically communicates with the outer-side outer conductors 161g2 and 163g2 maintained at the ground potential PVE of the electric wires 161 and 163.

The measurement control circuit 220 has a built-in regulator power supply PS. The regulator power supply PS is driven by an external battery BT through a power supply wiring BC. A portion of electricity input to the measurement control circuit 220 through the regulator power supply PS is distributed to the ion source power supply circuit 210 and the auxiliary electrode power supply circuit 240 via the insulated transformer 270. The measurement control circuit 220 also has a microprocessor 221 to thereby be able to communicate, through a communication line CC, with a control unit ECU adapted to control an internal combustion engine and thus can send signals indicative of results of measurement (magnitude of the signal current Is) by the aforementioned signal current detection circuit 230, etc., to the control unit ECU.

Next, the electrical function and operation of the particulate detection system 1 will be described (see FIGS. 1 and 3). The discharge electrode member 130 of the ceramic element 120 is connected to and electrically communicates with the second output terminal 212 of the ion source power supply circuit 210 through the discharge potential lead wire 162 of the electric wire 161 to thereby be maintained at the second potential PV2. Meanwhile, the auxiliary electrode member 140 of the ceramic element 120 is connected to and electrically communicates with the auxiliary second output terminal 242 of the auxiliary electrode power supply circuit 240 through the auxiliary potential lead wire 164 of the electric wire 163 to thereby be maintained at the auxiliary electrode potential PV3. Further, the inner metallic member 20 is connected to and electrically communicates with the inner circuit case 250, etc., through the inner-side outer conductors 161g1 and 163g1 of the electric wires 161 and 163 to thereby be maintained at the first potential PV1. Additionally, the outer metallic member 70 is connected to and electrically communicates with the outer circuit case 260, etc., through the outer-side outer conductors 161g2 and 163g2 of the electric wires 161 and 163 to thereby be maintained at the ground potential PVE.

The second potential PV2 of a positive high voltage (e.g., 1 kV to 2 kV) is applied from the ion source power supply circuit 210 of the circuit section 200 to the needle-shaped electrode portion 131 of the discharge electrode member 130 through the discharge potential lead wire 162 of the electric wire 161, the discharge potential terminal 46, and the discharge potential pad 135. As a result, gaseous discharge; specifically, corona discharge, occurs between a needle-shaped distal end portion 131ss of the needle-shaped electrode portion 131 and the inner protector 60 maintained at the first potential PV1, whereby ions CP are generated around the needle-shaped distal end portion 131ss. As described above, by the action of the gas introduction pipe 25, the exhaust gas EG is introduced into the interior of the inner protector 60, and a flow of the introduced gas EGI from the proximal end side GK toward the distal end side GS is produced near the ceramic element 120. Therefore, the generated ions CP adhere to particulates S contained in the introduced gas EGI. As a result, the particulates S become positively charged particulates SC, which flow toward the gas discharge opening 60e together with the introduced gas EGI, and are discharged into the exhaust pipe EP.

Meanwhile, a predetermined potential (e.g., a positive DC potential of 100 V to 200 V) is applied from the auxiliary electrode power supply circuit 240 of the circuit section 200 to the auxiliary electrode portion 141 of the auxiliary electrode member 140 through the auxiliary potential lead wire 164 of the electric wire 163, the auxiliary potential terminal 47, and the auxiliary potential pad 147 so that the auxiliary electrode portion 141 is maintained at the auxiliary electrode potential PV3. Thus, a repulsive force directed from the auxiliary electrode portion 141 toward the inner protector 60 (collection electrode) located on the radially outward side GDO acts on floating ions CPF, which are some of the generated ions CP and have not adhered to the particulates S. As a result, the floating ions CPF are caused to adhere to various portions of the collection electrode (inner protector 60), whereby collection of the floating ions CPF by the collection electrode is assisted. Thus, the floating ions CPF can be collected reliably, and the floating ions CPF are prevented from being discharged through the gas discharge opening 60e.

In the particulate detection system 1, the signal current detection circuit 230 detects a signal (signal current Is) corresponding to the amount of charge of discharged ions CPH adhering to the charged particulates SC which are discharged through the gas discharge opening 60e. As a result, the amount (concentration) of the particulates S contained in the exhaust gas EG can be detected. As described above, according to the present embodiment, the ions CP are caused to adhere to the particulates S contained in the exhaust gas EG introduced into the gas introduction pipe 25 to thereby produce the charged particulates SC, and the amount of the particulates S contained in the exhaust gas EG is detected by using the signal current Is which flows between the first potential PV1 and the ground potential PVE in accordance with the amount of the charged particulates SC.

Further, in the particulate sensor 10, the ceramic element 120 has the element heater 150. The heater pad 156 of the element heater 150 electrically communicates with the energization terminal 225a of the second heater energization circuit 225 of the circuit section 200 through the heater terminal 48 and the heater lead wire 174 of the electric wire 173. Also, the heater pad 158 of the element heater 150 electrically communicates with the energization terminal 225b of the second heater energization circuit 225 through the heater terminal 49 and the heater lead wire 176 of the electric wire 175.

Thus, when the second heater energization circuit 225 applies a predetermined heater energization voltage between the heater pad 156 and the heater pad 158, the heat generation resistor 151 of the element heater 150 is energized and thus generates heat. As a result, since foreign substances, such as water droplets and soot, adhering to the ceramic element 120 can be removed by means of heating the ceramic element 120, the insulation of the ceramic element 120 can be recovered or maintained.

Additionally, in the particulate sensor 10 of the present embodiment, the first insulating spacer 100 has the spacer heater 105. The first heater terminal 107 of the spacer heater 105 electrically communicates with the energization terminal 223a of the first heater energization circuit 223 of the circuit section 200 through the heater metal connection member 85 and the heater lead wire 172 of the electric wire 171. Also, the second heater terminal 108 of the spacer heater 105 electrically communicates with the ground potential PVE and with the energization terminal 223b of the first heater energization circuit 223 through the outer metallic member 70 and the outer-tube metal connection member 95.

Thus, when the first heater energization circuit 223 applies a predetermined heater energization voltage between the first heater terminal 107 and the second heater terminal 108, the heat generation resistor 106 of the spacer heater 105 is energized and thus generates heat. As a result, by means of heating the spacer distal end portion 101 of the first insulating spacer 100, foreign substances, such as water droplets and soot, adhering to the gas contact portion 101s of the spacer distal end portion 101 can be removed (evaporated or burned out). Therefore, the particulate sensor 10 can recover or maintain the insulation of the first insulating spacer 100 interposed between the inner metallic member 20 maintained at the first potential PV1 and the outer metallic member 70 maintained at the ground potential PVE and thus can properly detect the amount of particulates S contained in the exhaust gas EG.

Also, since the heat generation resistor 106 of the spacer heater 105 is embedded in the first insulating spacer 100, there can be restrained a failure to properly energize the spacer heater 105 and a deterioration of the heat generation resistor 106 which could otherwise result from adhesion (accumulation) of foreign substances such as soot to the heat generation resistor 106. Therefore, even in the case of use of the particulate sensor 10 over a long period of time, heating by the spacer heater 105 can be maintained in a good condition.

Further, in the present embodiment, the first heater terminal 107 of the spacer heater 105 is provided on the outer shoulder surface (spacer contact surface) 102s, which comes into contact with the outer metallic member 70 (the stepped portion 83 of the mounting metallic member 80), of the first insulating spacer 100; and accordingly, the first heater terminal 107 electrically communicates with the outer metallic member 70. By virtue of such a structure, a lead wire or the like for connecting the first heater terminal 107 to the outer metallic member 70 can be eliminated, so that the particulate sensor 10 can have a simple structure, and the first heater terminal 107 can electrically communicate with the outer metallic member 70 in a reliable manner. Also, in the present embodiment, the first heater terminal 107 is formed annularly on the outer shoulder surface 102s to extend in the circumferential direction CD of the first insulating spacer 100 and thus is in contact with the outer metallic member 70 (the stepped portion 83 of the mounting metallic member 80) over the entire circumference thereof. As a result, the first heater terminal 107 and the outer metallic member 70 can be electrically connected to each other in a more reliable manner.

Particularly, in the particulate sensor 10, the signal current Is is small; however, since a deterioration in insulation of the first insulating spacer 100 interposed between the inner metallic member 20 maintained at the first potential PV1 and the outer metallic member 70 maintained at the ground potential PVE can be restrained by means of the spacer heater 105, a leak current between the first potential PV1 and the ground potential PVE can be restrained, whereby the small signal current Is flowing therebetween can be properly detected. As a result, the amount of the particulates S contained in the exhaust gas EG can be properly detected.

(Second Embodiment)

Figure 9:
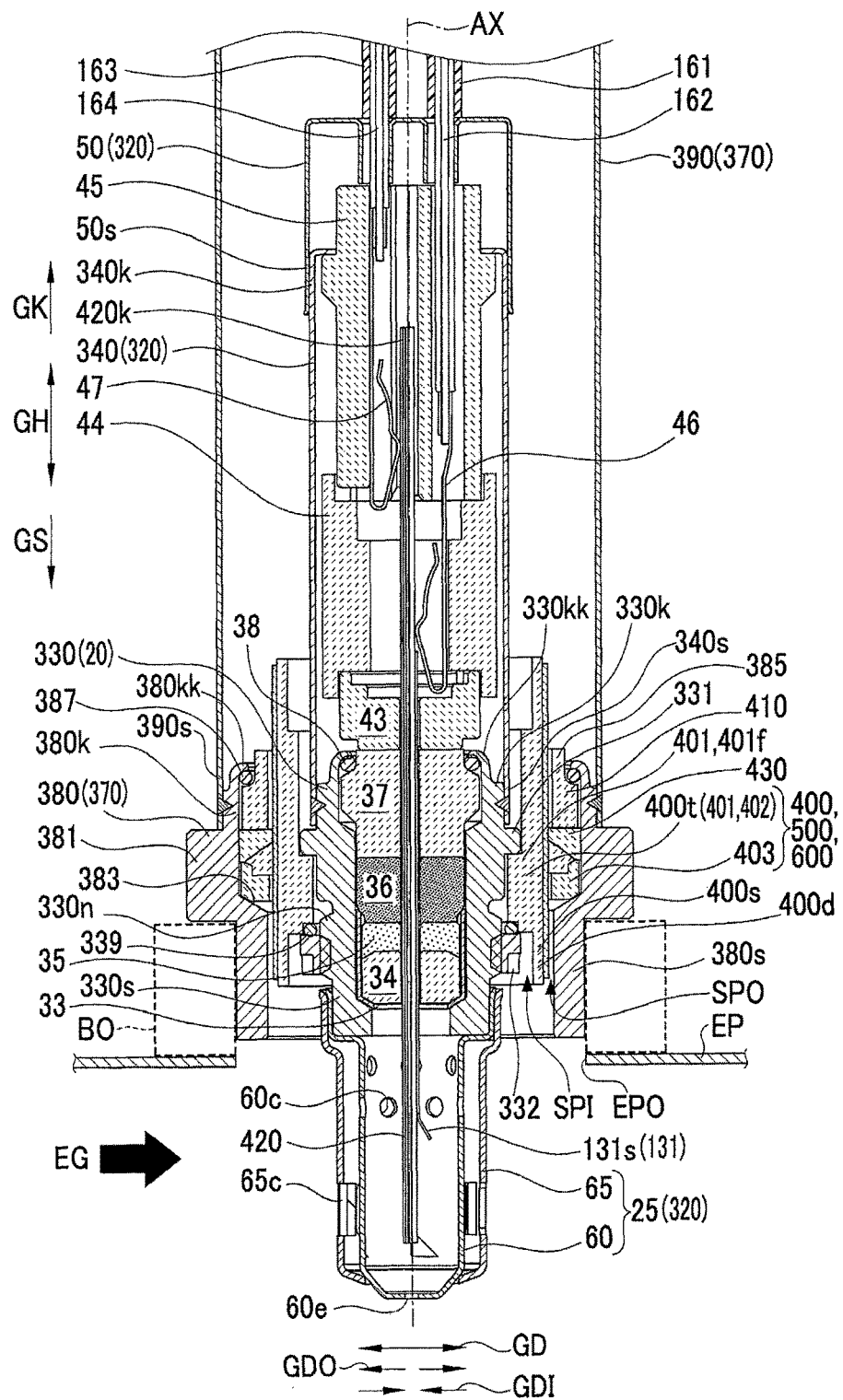
FIG. 9 is a longitudinal sectional view of a particulate sensor according to a second embodiment of the present invention.
Figure 10:
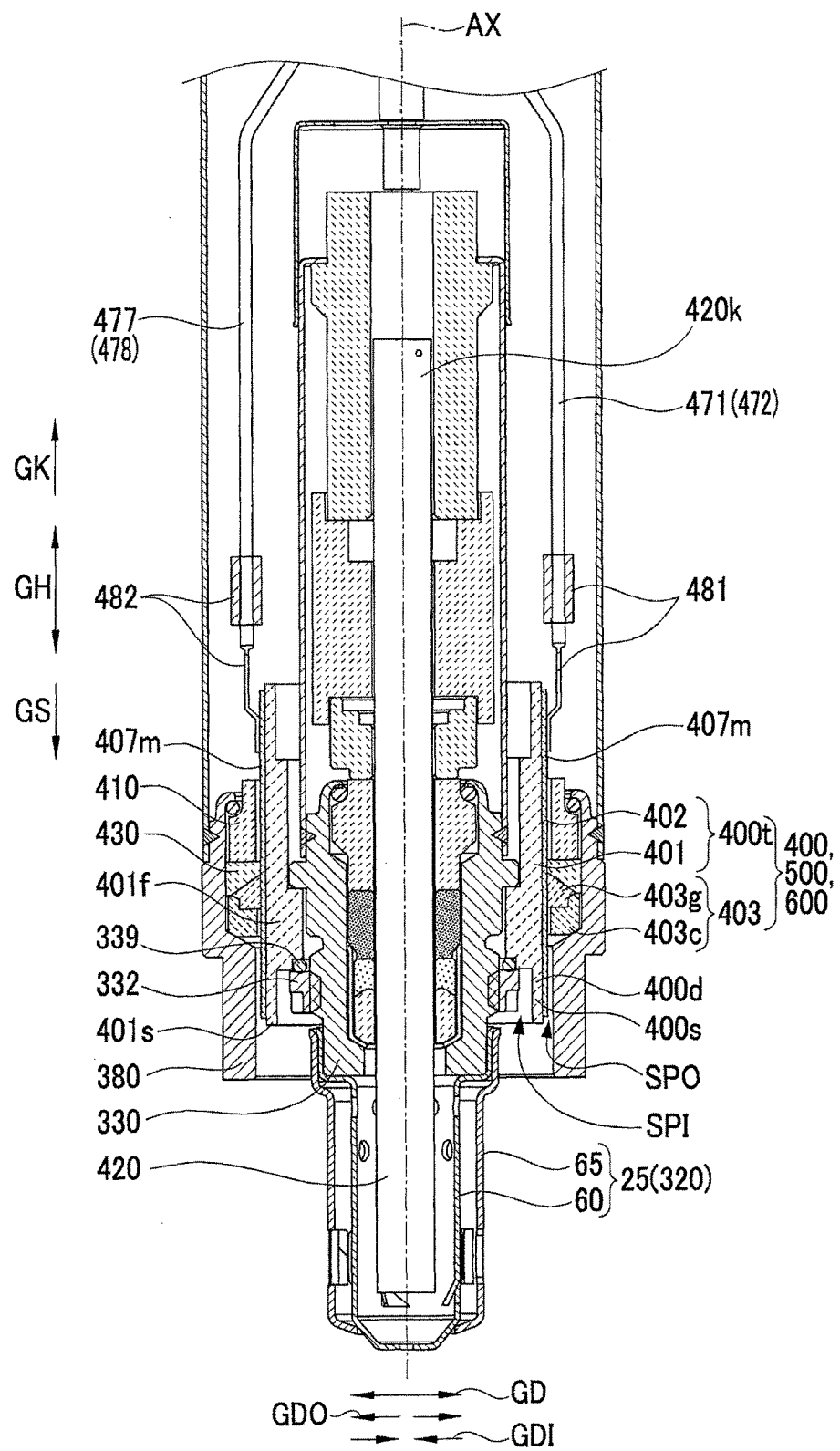
FIG. 10 is a longitudinal sectional view of the particulate sensor according to the second embodiment as viewed in a rotated profile produced by rotating FIG. 9 90 degrees about an axial line.
Figure 11:
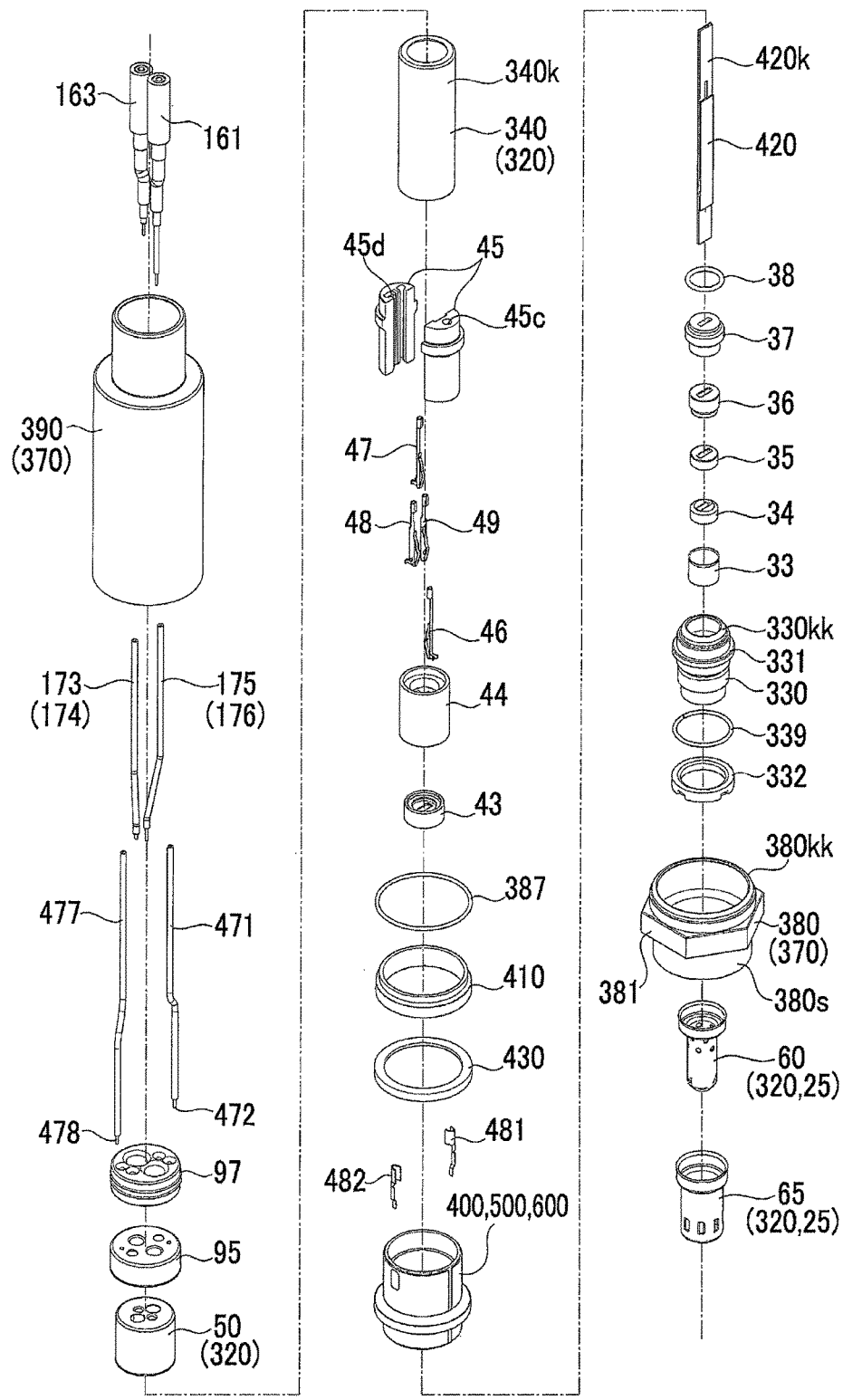
FIG. 11 is an exploded perspective view of the particulate sensor according to the second embodiment.

Next, a second embodiment of the present invention will be described with reference to the drawings. A particulate detection system 301 of the second embodiment is composed of a particulate sensor 310 (see FIGS. 9 to 11) and the circuit section 200 (see FIG. 3), which is in common with the first embodiment, and detects the amount of particulates S contained in the exhaust gas EG flowing through the exhaust pipe EP. In FIGS. 9 and 10, in the longitudinal direction GH along the axial line AX of the particulate sensor 310, the lower side in the drawings corresponds to the distal end side GS, and the opposite upper side in the drawings corresponds to the proximal end side GK. Since a form at the proximal end side of the particulate sensor 310 is substantially similar to that of the particulate sensor 10 of the first embodiment, a portion at the proximal end side is eliminated from FIGS. 9 and 10. The particulate sensor 310 will be described, centering on features different from those of the particulate sensor 10 of the first embodiment; and components similar to those of the particulate sensor 10 are denoted by like reference numerals, and description thereof is omitted or briefed.

The particulate sensor 310 is attached such that the gas introduction pipe 25 of its inner metallic member 320 is disposed within the metal exhaust pipe EP maintained at the ground potential PVE through the mounting opening EPO of the exhaust pipe EP. The ions CP are caused to adhere to the particulates S contained in the introduced gas EGI introduced into the gas introduction pipe 25 through the gas introduction holes 65c to thereby produce the charged particulates SC, and the charged particulates SC, together with the introduced gas EGI, are discharged into the exhaust pipe EP through the gas discharge opening 60e (see FIG. 8). The particulate sensor 310 is composed of the inner metallic member 320 including the gas introduction pipe 25, an outer metallic member 370, an insulating spacer 400, a ceramic element 420, etc.

The inner metallic member 320 is maintained at the first potential PV1 different from the ground potential PVE and is composed of a metallic shell 330, an inner tube 340, the inner-tube metal connection member 50, and the gas introduction pipe 25 (the inner protector 60 and the outer protector 65).

The metallic shell 330 assumes a form substantially similar to that of the metallic shell 30 of the particulate sensor 10 according to the first embodiment described above. However, in contrast to the particulate sensor 10, the metallic shell 330 has a male screw portion 330n between a flange 331 and a distal end portion 330s. A spacer retaining ring 332 for retaining the insulating spacer 400 (to be described later) through a line packing 339 is threadingly engaged with the male screw portion 330n. As a result, a thick wall portion 401f of a spacer main body 401 of the insulating spacer 400 is held between the flange 331 of the metallic shell 330 and the spacer retaining ring 332, whereby, as will be described later, the metallic shell 330 and the ceramic element 420, etc., held by the metallic shell 330 are fixed to a mounting metallic member 380 through the insulating spacer 400.

The ceramic element 420 slightly longer than the ceramic element 120 of the first embodiment extends through the metallic shell 330. Similar to the particulate sensor 10 of the first embodiment, in the interior of the metallic shell 330, the metal cup 33, the ceramic holder 34, the first powder charged layer 35, the second powder charged layer 36, the ceramic sleeve 37 are disposed in this order from the distal end side GS toward the proximal end side GK, and the crimp portion 330$kk$ presses the ceramic sleeve 37 toward the distal end side GS through the crimp ring 38.

The ceramic element 420 differs from the ceramic element 120 in that a dimension along the longitudinal direction GH is slightly longer. However, other component forms and structures are similar to those of the ceramic element 120 described above (see FIGS. 6 and 7); therefore, description of the ceramic element 420 is eliminated from description of the second embodiment.

In contrast to the inner tube 40 of the first embodiment, a distal end portion 340$s$ of the inner tube 340 is fitted onto a proximal end portion 330$k$ of the metallic shell 330 and is laser-welded to the proximal end portion 330$k$. Similar to the inner tube 40 of the first embodiment, in the interior of the inner tube 340, the insulating holder 43, the first separator 44, and the second separator 45 are disposed in this order from the distal end side GS toward the proximal end side GK. The ceramic element 420 extends through the insulating holder 43 and the first separator 44. Meanwhile, the second separator 45 accommodates an element proximal-end portion 420$k$ of the ceramic element 420. Similar to the first embodiment, the inner-tube metal connection member 50 is fitted onto a proximal end portion 340$k$ of the inner tube 340, and the distal end portion 50$s$ of the inner-tube metal connection member 50 is laser-welded to the proximal end portion 340$k$ of the inner tube 340. Similar to the first embodiment, the gas introduction pipe 25 is composed of the inner protector 60 and the outer protector 65, surrounds a distal end portion of the ceramic element 420 from the radially outward side GDO to thereby protect the ceramic element 420 from water droplets and foreign substances as well as introduce the exhaust gas EG to a space around the ceramic element 420.

Next, the outer metallic member 370 will be described. The outer metallic member 370 is greater in diameter than the outer metallic member 70 of the particulate sensor 10 according to the first embodiment described above, but assumes a form substantially similar to that of the outer metallic member 70 in such a manner as to circumferentially surround the inner metallic member 320 from the radial direction GD while being separated from the inner metallic member 320 and be attached to the exhaust pipe EP to thereby be maintained at the ground potential PVE. The outer metallic member 370 is composed of the mounting metallic member 380 and an outer tube 390.

The mounting metallic member 380 is disposed around the metallic shell 330 and around a distal end portion of the inner tube 340 in such a manner as to be separated from them in the radial direction GD. The mounting metallic member 380 has a flange portion 381 having a hexagonal columnar shape, and a stepped portion 383. The mounting metallic member 380 also has a male screw (not shown) used for fixation to the exhaust pipe EP and formed on the outer circumference of its distal end portion 380$s$, and the particulate sensor 310 is fixed to the exhaust pipe EP via the attachment boss BO by means of the male screw of the distal end portion 380$s$.

In the particulate sensor 10 of the first embodiment, the first insulating spacer 100 and the second insulating spacer 110 separate and electrically insulate the mounting metallic member 80 and the inner metallic member 20 from each other. However, in the particulate sensor 310 of the second embodiment, the single insulating spacer 400 electrically insulates the outer metallic member 370 and the inner metallic member 320; particularly, the mounting metallic member 380 and the metallic shell 330, from each other. A crimp portion 380$kk$, located furthest toward the proximal end side GK, of the mounting metallic member 380 is crimped toward the radially inward side GDI, thereby pressing a pressing sleeve 410 through a line packing 387 toward the distal end side GS and pressing an annular protrusion member 403 of the insulating spacer 400 through a powder charged member 430 toward the distal end side GS and thus against the stepped portion 383 of the mounting metallic member 380 and thus fixing the insulating spacer 400 to the mounting metallic member 380. Meanwhile, similar to the outer tube 90 of the particulate sensor 10, a distal end portion 390$s$ of the outer tube 390 is fitted onto a proximal end portion 380$k$ of the mounting metallic member 380 and is laser-welded to the proximal end portion 380$k$.

Next, the insulating spacer 400 will be described (see also FIGS. 12 to 16). The insulating spacer 400 is a cylindrical member formed primarily of alumina and extending in the longitudinal direction GH. As mentioned above, the insulating spacer 400 intervenes between the inner metallic member 320 and the outer metallic member 370 to thereby electrically insulate them from each other. Specifically, the insulating spacer 400 is disposed between the inner metallic member 320; i.e., the metallic shell 330 as well as a distal end portion of the inner tube 340, and the outer metallic member 370; i.e., the mounting metallic member 380 as well as a distal end portion of the outer tube 390. The insulating spacer 400 is composed of a substantially cylindrical tubular member 400$t$ and an annular protrusion member 403 protruding annularly from the tubular member 400$t$ toward the radially outward side GDO.

Figure 13:
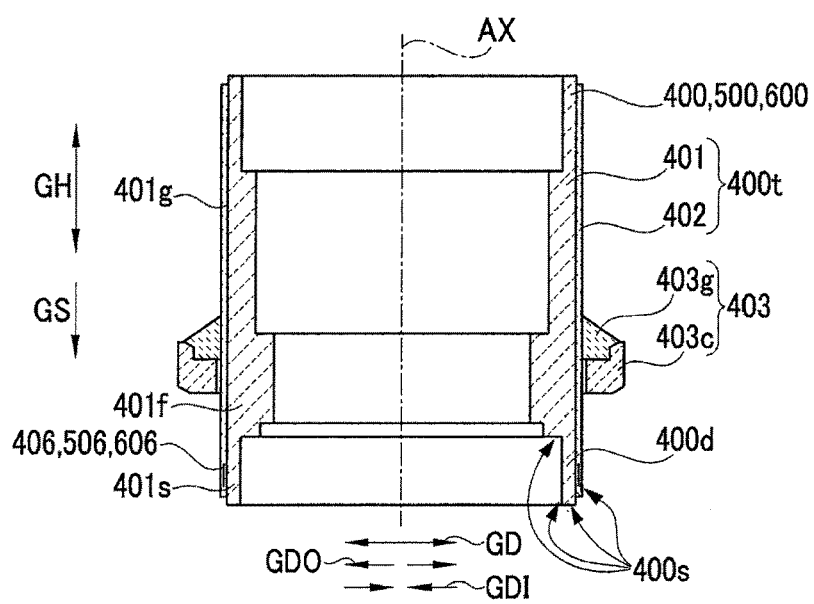
FIG. 13 is a longitudinal sectional view of the insulating spacer according to the second embodiment.
Figure 14:
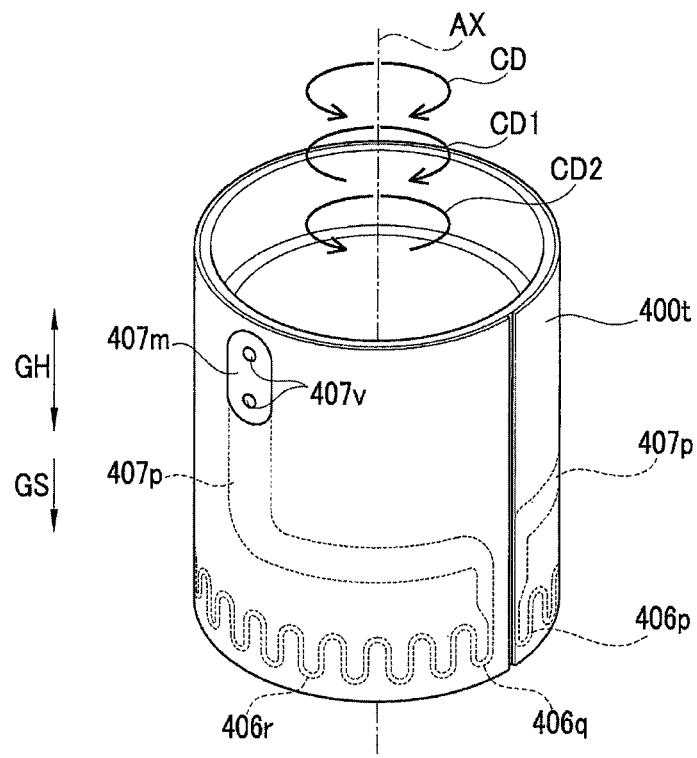
FIG. 14 is a perspective view of the insulating spacer according to the second embodiment as viewed before formation of an annular protrusion member.
Figure 15:
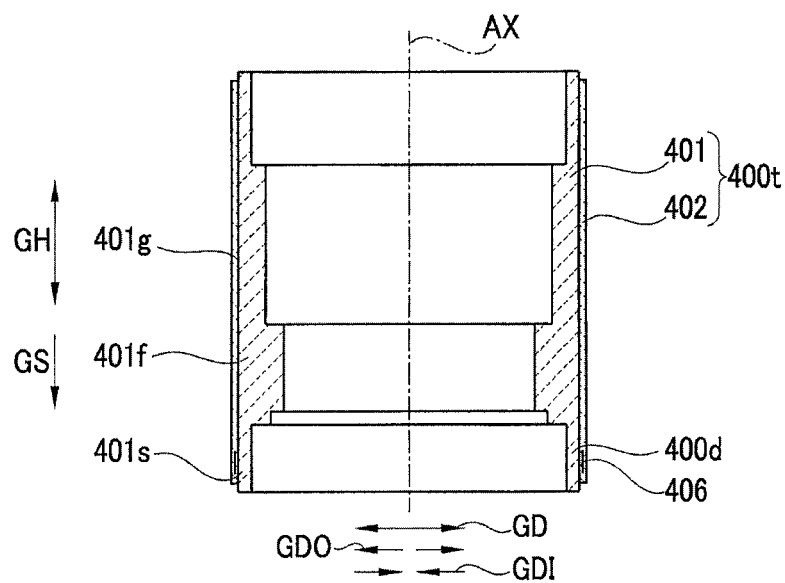
FIG. 15 is a longitudinal sectional view of the insulating spacer according to the second embodiment as viewed before formation of the annular protrusion member.

A portion at the distal end side GS of the tubular member 400$t$ of the insulating spacer 400 serves as a gas contact portion 400$s$ which is exposed to the interior of the exhaust pipe EP and comes into contact with the exhaust gas EG in a state in which the particulate sensor 310 is attached to the exhaust pipe EP (see FIGS. 9 and 13).

The insulating spacer 400 has a cylindrical spacer main body 401 formed of alumina and serving as the tubular member 400$t$, a laminar heater section 402 which is wound on a cylindrical outer circumferential surface 401$g$ of the spacer main body 401 in a cylindrical single-layer (shape resembling letter C) manner with a gap formed between opposite ends to avoid overlap, and the annular protrusion member 403 which is gastightly fitted onto the laminar heater section 402 and protrudes toward the radially outward side GDO of the insulating spacer 400. The spacer main body 401 has the thick wall portion 401$f$ located toward the distal end side GS in the longitudinal direction GH along the axial line AX, and a distal-end thin wall portion 401$s$ located on the distal end side GS of the thick wall portion 401$f$.

Figure 16:
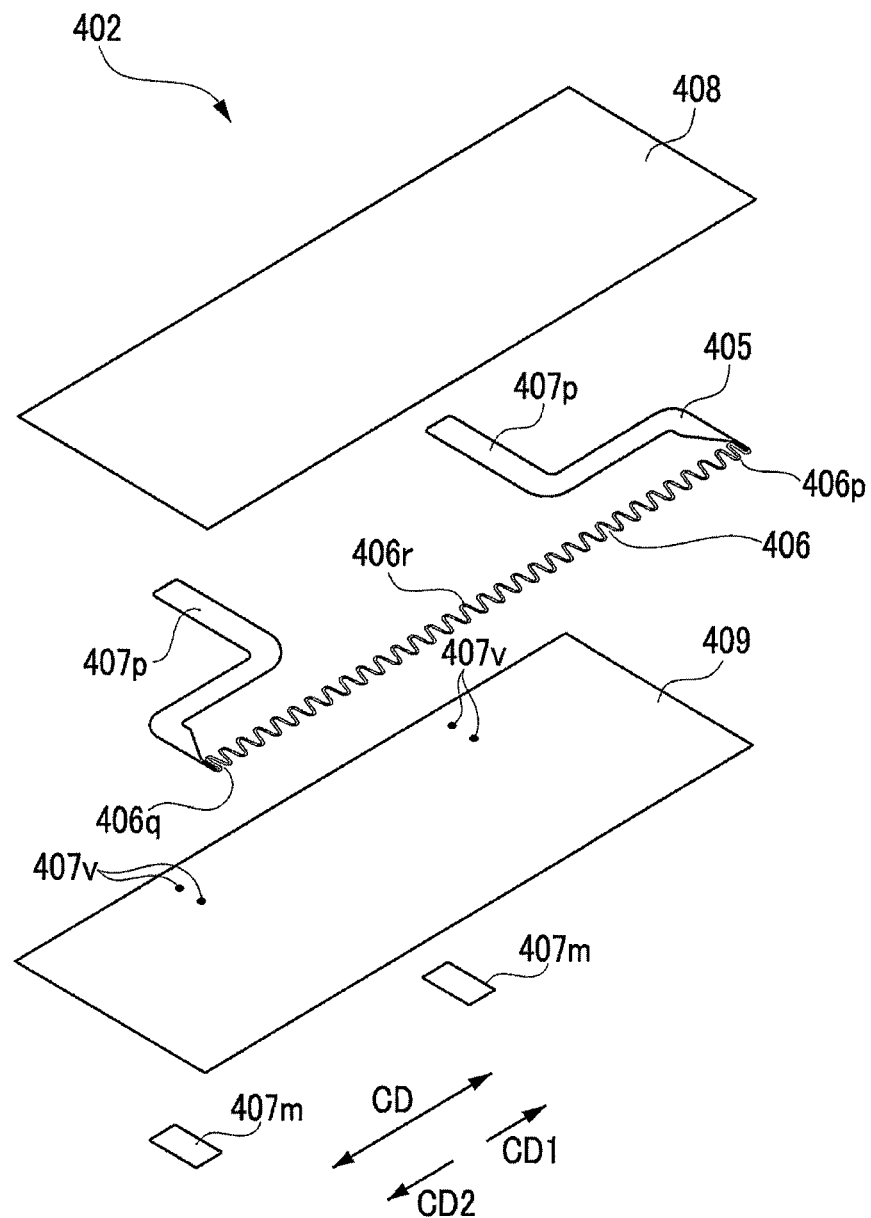
FIG. 16 is an exploded perspective view of a developed laminar heater section of the insulating spacer according to the second embodiment.
Figure 17:
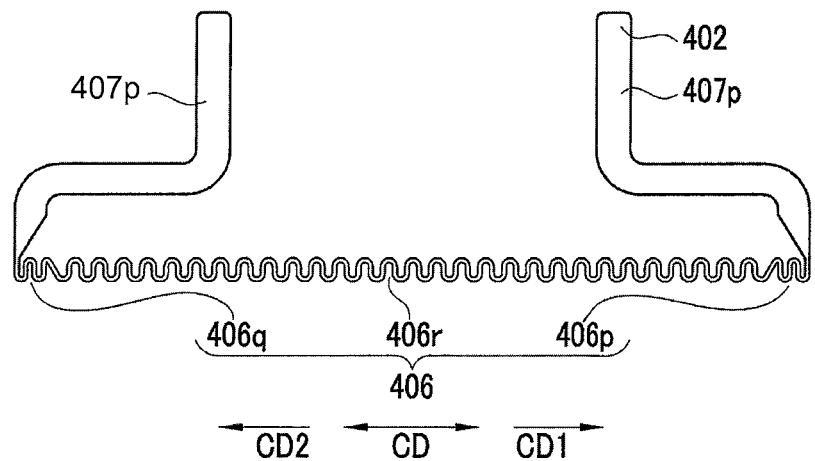
FIG. 17 is a plan view of a developed spacer heater of the laminar heater section according to the second embodiment.

Meanwhile, as shown in FIG. 16, the laminar heater section 402 is composed of a laminar spacer heater 405, a base insulating layer 408 formed of alumina and located internally of the laminar spacer heater 405, and a cover insulating layer 409 formed of alumina and located externally of the spacer heater 405. The spacer heater 405 (see FIGS. 16 and 17) is composed of a laminar heat generation resistor 406 formed of tungsten, and heater lead portions 407. The heater lead portions 407 are composed of lead main bodies 407$p$ extending from respective opposite ends of the laminar heat generation resistor 406, terminal pads 407$m$ exposed on the surface of the laminar heater section 402, and via conductors 407$v$ extending through the cover insulating layer 409 for establishing electrical communication between the lead main bodies 407*p* and the terminal pads 407*m*.

Figure 12:
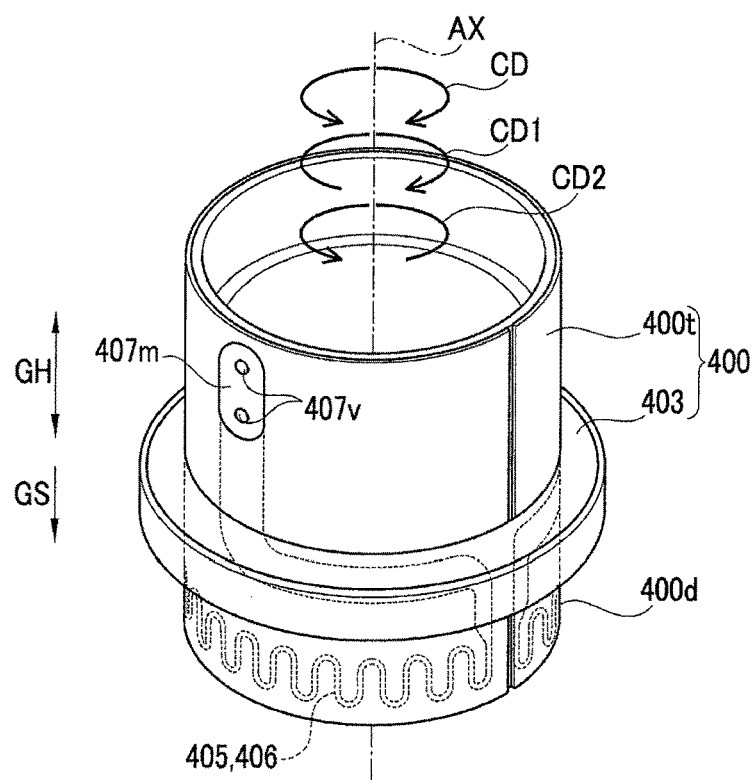
FIG. 12 is a perspective view of an insulating spacer according to a second embodiment of the present invention.

The laminar heat generation resistor 406 extends in the circumferential direction CD (horizontal direction in FIG. 17) of the insulating spacer 400. As a result of the laminar heat generation resistor 406 being wound around the spacer main body 401, as shown in FIG. 12, one end portion 406*p* located on one side CD1 (right side in FIG. 17) and the other end portion 406*q* located on the other side CD2 (left side in FIG. 17) are disposed to face each other in the circumferential direction CD and be close to each other. Also, the laminar heat generation resistor 406 is formed in a meandering (zigzag) manner. However, the one end portion 406*p* and the other end portion 406*q* are formed at a smaller bending pitch than is a central portion 406*r* located therebetween; thus, as compared with the central portion 406*r*, the one end portion 406*p* and the other end portion 406*q* are more likely to generate heat; i.e., the one end portion 406*p* and the other end portion 406*q* generate a large amount of heat per unit length in the circumferential direction CD. As a result, since the surface temperatures of those portions of the insulating spacer 400 which correspond to the one end portion 406*p* and the other end portion 406*q* can be increased, there is prevented a failure to remove foreign substances, such as water droplets and soot, adhering to and a resultant occurrence of a deterioration in insulation in a portion corresponding to the gap between the one end portion 406*p* and the other end portion 406*q* (a region which is located on the one side CD1 of the one end portion 406*p* in the circumferential direction CD and on the other side CD2 of the other end portion 406*q* in the circumferential direction CD and in which the laminar heat generation resistor 406 does not exist). The failure to remove foreign substances could otherwise result from a drop in the surface temperature of the portion corresponding to the gap.

Further, in the insulating spacer 400 of the second embodiment, the laminar heat generation resistor 406 of the laminar heater section 402 is disposed at the radially outward side GDO of the distal-end thin wall portion 401*s* of the spacer main body 401. Thus, as shown in FIGS. 9 and 10, a separated portion 400*d* included in the gas contact portion 400*s* and composed of the distal-end thin wall portion 401*s* and a portion (a portion including the laminar heat generation resistor 406) of the laminar heater section 402 located on the radially outward side GDO of the distal-end thin wall portion 401*s* is separated from the inner metallic member 320 (the metallic shell 330 and the spacer retaining ring 332) located on the radially inward side GDI of the separated portion 400*d* with an inner space SPI formed therebetween. Additionally, the separated portion 400*d* is separated from the outer metallic member 370 (the distal end portion 380*s* of the mounting metallic member 380) located on the radially outward side GDO of the separated portion 400*d* with an outer space SPO formed therebetween. As a result, the separated portion 400*d* is small in heat capacity, and the spaces SPO and SPI restrain heat conduction from the separated portion 400*d* to the inner metallic member 320 and to the outer metallic member 370; therefore, the separated portion 400*d* readily has a high temperature by means of the laminar heat generation resistor 406 generating heat through energization of the laminar heater section 402, whereby accumulated foreign substances, such as water droplets and soot, can be readily removed, and the accumulation of foreign substances can be prevented.

The annular protrusion member 403 is an annular member formed of alumina and is composed of a ceramic ring 403*c* fitted onto the laminar heater section 402 provided on the tubular member 400*t*; specifically, on the outer circumference of the spacer main body 401, and a glass seal member 403*g* formed of glass and adapted to gastightly fix the ceramic ring 403*c* to the laminar heater section 402. As a result of the crimp portion 380*kk* of the mounting metallic member 380 being crimped, the annular protrusion member 403 of the insulating spacer 400 is pressed toward the distal end side GS through the line packing 387, the pressing sleeve 410, and the powder charged member 430 to thereby be pressed against the stepped portion 383 of the mounting metallic member 380. Thus, according to the second embodiment, by virtue of the insulating spacer 400 having the annular protrusion member 403, the insulating spacer 400 can be readily and gastightly fixed to the mounting metallic member 380.

In formation of the insulating spacer 400, a green laminar heater section 402 including therein the laminar heat generation resistor and the lead main bodies 407*p* formed by pattern printing is wound on the outer circumference of a calcined spacer main body 401, followed by firing. Subsequently, the ceramic ring 403*c* is fitted onto the laminar heater section 402 and is then gastightly fixed to the laminar heater section 402 by means of glass to thereby provide the glass seal member 403*g*.

As shown in FIG. 10, the two heater lead portions 407 of the laminar heater section 402 of the insulating spacer 400 are connected respectively to heater lead wires 472 and 478 which are core wires of single-core electric wires 471 and 477, through connection terminals 481 and 482. Specifically, a distal end portion of the heater lead wire 472 of the electric wire 471 and a distal end portion of the heater lead wire 478 of the electric wire 477 are held respectively by the connection terminals 481 and 482 brazed to the respective terminal pads 407*m* to thereby electrically communicate with the connection terminals 481 and 482. As shown in FIG. 3, the energization terminal 223*a* of the first heater energization circuit 223 is connected to the electric wire 471 (heater lead wire 472), and the energization terminal 223*b* is connected to the heater lead wire 478 of the electric wire 477; therefore, the first heater energization circuit 223 can energize the spacer heater 405 (laminar heat generation resistor 406).

Thus, by means of the first heater energization circuit 223 energizing the laminar heat generation resistor 406 to generate heat and thus heat the separated portion 400*d* of the insulating spacer 400, foreign substances, such as water droplets and soot, adhering to the gas contact portion 400*s* located at the distal end side of the insulating spacer 400 can be removed (evaporated or burned out). Therefore, the particulate sensor 310 can recover or maintain the insulation of the insulating spacer 400 interposed between the inner metallic member 320 (metallic shell 330) maintained at the first potential PV1 and the outer metallic member 370 (mounting metallic member 380) maintained at the ground potential PVE and thus can properly detect the amount of particulates S contained in the exhaust gas EG.

Also, since the laminar heat generation resistor 406 of the spacer heater 405 is embedded in the insulating spacer 400 and is covered with the cover insulating layer 409, there can be restrained a failure to properly energize the spacer heater 405 and a deterioration of the laminar heat generation resistor 406 which could otherwise result from adhesion (accumulation) of foreign substances such as soot to the laminar heat generation resistor 406. Therefore, even in the case of use of the particulate sensor 310 over a long period of time, heating by the spacer heater 405 can be maintained in a good condition.

In contrast to the particulate sensor 10 of the first embodiment which uses five electric wires 161, 163, 171, 173, and 175; specifically, two triple coaxial cables 161 and 163 and three single-core electric wires 171, 173, and 175, the particulate sensor 310 of the second embodiment uses six electric wires; specifically, the above-mentioned electric wires 471 and 477 in addition to the electric wires 161, 163, 173, and 175. However, since the outer-tube metal connection member 95, the grommet 97, etc., are substantially similar in form and structure to those of the first embodiment, description thereof is omitted. Also, as shown by the broken line in FIG. 3, in contrast to the first embodiment, the electric wire 477 is connected to the energization terminal 223b of the first heater energization circuit 223. However, since connections of the electric wires 161, 163, 173, 175, and 471 to the circuits of the circuit section 200 are similar to corresponding connections of the first embodiment, description thereof is omitted.

(First Modified Embodiment)

Figure 18:
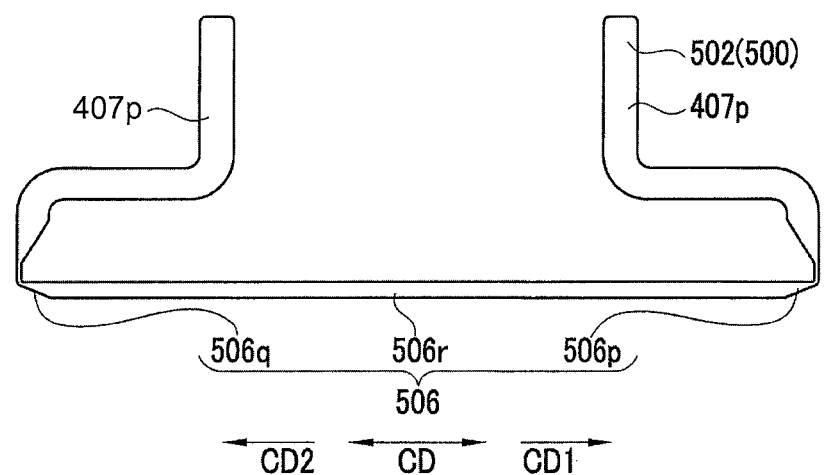
FIG. 18 is a plan view of a developed spacer heater of a laminar heater section according to a first modified embodiment of the present invention.

In the particulate sensor 310 according to the second embodiment described above, the laminar heat generation resistor 406 of the laminar heater section 402 of the insulating spacer 400 has a meandering shape along the entire circumference in the circumferential direction CD. However, the laminar heat generation resistor can assume a different form. A laminar heat generation resistor 506 of a laminar heater section 502 of an insulating spacer 500 according to a first modified embodiment of the present invention (see FIG. 18) has a central portion 506r in a rectilinear strip shape as well as one end portion 506p and the other end portion 506q which are provided at opposite ends of the central portion 506r and whose width reduces outward. As a result of employment of this form, the entire resistance of the laminar heat generation resistor 506 can be reduced, whereby as compared with the particulate sensor 310 of the second embodiment which uses the laminar heat generation resistor 406, the laminar heat generation resistor 506 can be caused to generate heat at a low voltage and a large current.

(Second Modified Embodiment)

Figure 19:
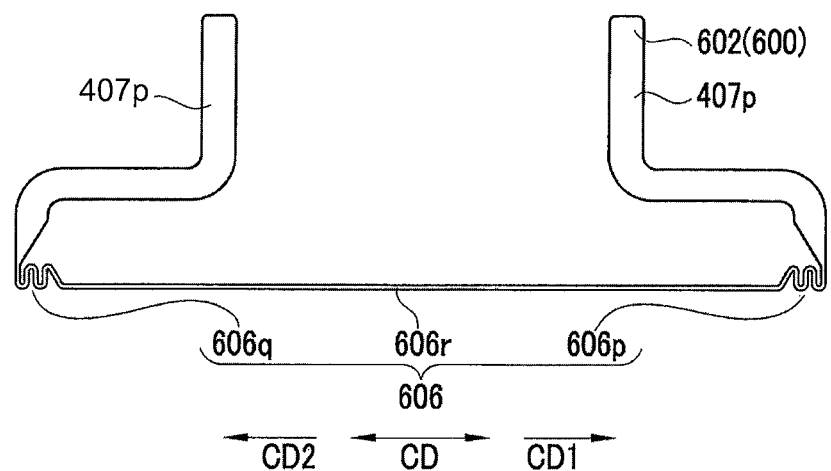
FIG. 19 is a plan view of a developed spacer heater of a laminar heater section according to a second modified embodiment of the present invention.

A laminar heat generation resistor 606 of a laminar heater section 602 of an insulating spacer 600 according to a second modified embodiment of the present invention (see FIG. 19) has a central portion 606r in a rectilinear strip shape as well as one end portion 606p and the other end portion 606q, both in a meandering shape, provided at opposite ends of the central portion 606r. As a result of employment of even this form, as compared with the laminar heat generation resistor 406 of the second embodiment, the entire resistance of the laminar heat generation resistor 606 can be reduced, whereby the laminar heat generation resistor 606 can be caused to generate heat at a low voltage and a large current.

While the present invention has been described with reference to the first and second embodiments and the first and second modified embodiments, the present invention is not limited thereto, but may be modified as appropriate without departing from the gist of the invention. For example, the first and second embodiments, etc., use the heat generation resistor 106 formed of tungsten; however, material for the heat generation resistor 106 is not limited thereto. Other metal materials, such as platinum and molybdenum, and electrically conductive ceramic materials may be used.

DESCRIPTION OF REFERENCE NUMERALS 1, 301: particulate detection system
10, 310: particulate sensor
20, 320: inner metallic member
25: gas introduction pipe
30, 330: metallic shell
330n: male screw portion
332: spacer retaining ring
40, 340: inner tube
50: inner-tube metal connection member
60: inner protector
60e: gas discharge opening
65: outer protector
65c: gas introduction hole
70, 370: outer metallic member
80, 380: mounting metallic member (outer metallic member)
90, 390: outer tube (outer metallic member)
100: first insulating spacer (insulating spacer)
101: spacer distal end portion
101s: gas contact portion
102: spacer intermediate portion
102s: outer shoulder surface (spacer contact surface)
105: spacer heater (heater)
106: heat generation resistor
107: first heater terminal
108: second heater terminal
120, 420: ceramic element
130: discharge electrode member
140: auxiliary electrode member
400, 500, 600: insulating spacer
400s: gas contact portion
400d: separated portion
SPI: inner space
SPO: outer space
401: spacer main body
402, 502, 602: laminar heater section
403: annular protrusion member
405: spacer heater (heater)
406, 506, 606: laminar heat generation resistor
406p, 506p, 606p: one end portion (of laminar heat generation resistor)
406q, 506q, 606q: the other end portion (of laminar heat generation resistor)
406r, 506r, 606r: central portion (of laminar heat generation resistor)
409: cover insulating layer
SP1: inner space (space located radially inward of separated portion)
SP2: outer space (space located radially outward of separated portion)
200: circuit section
EP: exhaust pipe (gas flow pipe)
EG: exhaust gas (target gas)
EGI: introduced gas
S: particulate
PVE: ground potential
PV1: first potential
Is: signal current
AX: axial line (of particulate sensor)
GD: radial direction
GDO: radially outward side
GDI: radially inward side
CD: circumferential direction (of insulating spacer)
CD1: one side (in circumferential direction)
CD2: the other side (in circumferential direction)
CP: ion
SC: charged particulate

The invention claimed is:

1. A particulate sensor attached to a metal gas flow pipe through which a target gas containing particulates flows and which is maintained at a ground potential, said particulate sensor comprising:
   an inner metallic member which is maintained at a first potential different from the ground potential and which has a gas introduction pipe into which the target gas is introduced;
   a tubular outer metallic member which surrounds a radially outer circumference of the inner metallic member and which is attached to the gas flow pipe to thereby be maintained at the ground potential; and
   a tubular insulating spacer which is interposed between the inner metallic member and the outer metallic member so as to electrically insulate them from each other and which has a tubular gas contact portion being exposed to the interior of the gas flow pipe and contacting the target gas flowing through the gas flow pipe, wherein
   the insulating spacer has a heater that heats the gas contact portion, a tubular spacer main body formed of an insulating ceramic, and a laminar heater section covering an outer circumferential surface of the spacer main body and including the heater,
   the heater includes a heat generation resistor embedded in the insulating spacer, and
   the laminar heater section includes a laminar heat generation resistor extending in the circumferential direction of the insulating spacer and also includes a cover insulating layer which is formed of an insulating ceramic and covers the laminar heat generation resistor, wherein opposite end portions of the laminar heat generation resistor located on opposite sides in the circumferential direction are disposed to face each other in the circumferential direction and be close to each other.

2. The particulate sensor according to claim 1, wherein the laminar heat generation resistor of the laminar heater section is configured such that each of the opposite end portions of the laminar heat generation resistor generates a larger amount of heat per unit length in the circumferential direction as compared with a central portion of the laminar heat generation resistor located between the opposite end portions.

3. The particulate sensor according to claim 1, wherein the insulating spacer has an annular protrusion member which is formed of an inorganic insulating material, is gastightly fitted onto the laminar heater section, and protrudes outward in the radial direction of the insulating spacer.

4. The particulate sensor according to claim 1, wherein the gas contact portion of the insulating spacer includes a separated portion which is separated from the inner metallic member located radially inward of the gas contact portion with an inner space formed therebetween and is separated from the outer metallic member located radially outward of the gas contact portion with an outer space formed therebetween; and the heat generation resistor of the insulating spacer is located in the separated portion.

5. The particulate sensor according to claim 1, wherein ions generated by gaseous discharge are caused to adhere to the particulates contained in the target gas introduced into the interior of the gas introduction pipe to thereby produce charged particulates; and
   the amount of the particulates contained in the target gas is detected by using a signal current which flows between the first potential and the ground potential in accordance with the amount of the charged particulates.

6. The particulate sensor according to claim 1, wherein
   the heater has paired first and second heater terminals electrically communicating with the heat generation resistor; and
   the first heater terminal is formed on a spacer contact surface, which contacts the outer metallic member, and
   the first heater terminal electrically communicates with the outer metallic member.

7. The particulate sensor according to claim 6, wherein
   the spacer contact surface is an annular surface extending in a circumferential direction of the insulating spacer; and
   the first heater terminal is annularly formed on the spacer contact surface to extend in the circumferential direction of the insulating spacer and is in contact with the outer metallic member over the entire circumference thereof.

8. A particulate sensor attached to a metal gas flow pipe through which a target gas containing particulates flows and which is maintained at a ground potential, said particulate sensor comprising:
   an inner metallic member which is maintained at a first potential different from the ground potential and which has a gas introduction pipe into which the target gas is introduced;
   a tubular outer metallic member which surrounds a radially outer circumference of the inner metallic member and which is attached to the gas flow pipe to thereby be maintained at the ground potential; and
   a tubular insulating spacer which is interposed between the inner metallic member and the outer metallic member so as to electrically insulate them from each other and which has a tubular gas contact portion being exposed to the interior of the gas flow pipe and contacting the target gas flowing through the gas flow pipe, wherein
   the insulating spacer has a heater that heats the gas contact portion, and
   the heater includes a heat generation resistor embedded in the insulating spacer and paired first and second heater terminals electrically communicating with the heat generation resistor,
   the first heater terminal is formed on a spacer contact surface, which contacts the outer metallic member, and
   the first heater terminal electrically communicates with the outer metallic member.

* * * * *